(12) United States Patent
Gross

(10) Patent No.: US 12,090,066 B1
(45) Date of Patent: Sep. 17, 2024

(54) MULTI-PIECE IMPLANTABLE JOINT PROSTHESIS

(71) Applicant: Canary Medical Inc., Vancouver (CA)

(72) Inventor: Jeffrey M. Gross, Carlsbad, CA (US)

(73) Assignee: Canary Medical Inc., Vancouver (CA)

( * ) Notice: Subject to any disclaimer, the term of this patent is extended or adjusted under 35 U.S.C. 154(b) by 123 days.

(21) Appl. No.: 17/589,728

(22) Filed: Jan. 31, 2022

Related U.S. Application Data

(60) Provisional application No. 63/143,910, filed on Jan. 31, 2021.

(51) Int. Cl.
  *A61F 2/46* (2006.01)
  *A61B 5/00* (2006.01)
  *A61F 2/34* (2006.01)
  *A61F 2/36* (2006.01)
  *A61F 2/30* (2006.01)

(52) U.S. Cl.
  CPC .......... *A61F 2/4657* (2013.01); *A61B 5/0022* (2013.01); *A61B 5/4851* (2013.01); *A61F 2/34* (2013.01); *A61F 2/36* (2013.01); *A61F 2002/3067* (2013.01); *A61F 2002/4666* (2013.01); *A61F 2002/4668* (2013.01); *A61F 2002/467* (2013.01); *A61F 2002/4672* (2013.01); *A61F 2002/4674* (2013.01)

(58) Field of Classification Search
  CPC ........ A61F 2/36; A61F 2/3859; A61F 2/4607; A61F 2250/0096; A61B 90/06; A61B 2090/064; A61B 2090/067; A61B 17/74
  See application file for complete search history.

(56) References Cited

U.S. PATENT DOCUMENTS

| | | | | |
|---|---|---|---|---|
| 5,470,354 | A * | 11/1995 | Hershberger | A61F 2/4684 600/595 |
| 7,442,196 | B2 * | 10/2008 | Fisher | A61F 2/4657 606/88 |
| 7,458,989 | B2 * | 12/2008 | Banks | A61B 90/06 600/587 |
| 7,704,282 | B2 * | 4/2010 | Disilvestro | A61F 2/32 600/587 |
| 9,492,115 | B2 * | 11/2016 | Stein | A61B 5/0084 |
| 2003/0153924 | A1 * | 8/2003 | Kana | A61B 90/94 606/89 |
| 2004/0064073 | A1 * | 4/2004 | Heldreth | A61F 2/4657 600/595 |
| 2005/0010300 | A1 * | 1/2005 | Disilvestro | A61F 2/32 128/903 |

(Continued)

*Primary Examiner* — Anu Ramana

(57) ABSTRACT

A multi-piece implantable joint prosthesis includes an adapter to which at least two pieces are coupled, where the adapter has a coupler for coupling to a first piece and a different coupler for coupling to a second piece, where at least one piece, e.g., the first piece, may contain an electronic component such as a sensor that detects and measures movement of the prosthesis when the prosthesis is implanted in a patient, and can thus monitor the kinematic movement of the patient in real life situations, where the electronic component may also include a memory to store the data obtained by the sensor, and a communication interface to transmit the data to an external location where it may be analyzed, and a power source to provide power to the sensor, memory and communication interface.

8 Claims, 11 Drawing Sheets

(56) References Cited

U.S. PATENT DOCUMENTS

2005/0101962 A1* 5/2005 Schwenke ............. A61F 2/4607
                                                    606/86 R
2012/0191206 A1* 7/2012 Stein ...................... A61F 2/389
                                                    600/587

* cited by examiner

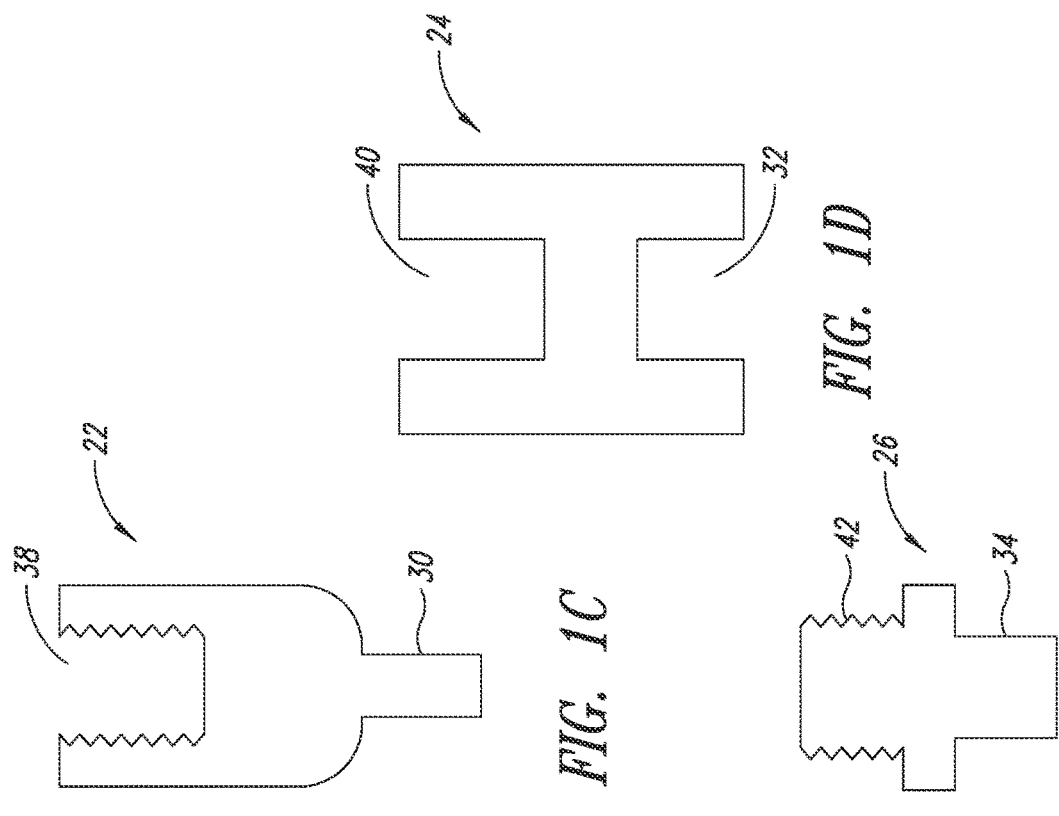
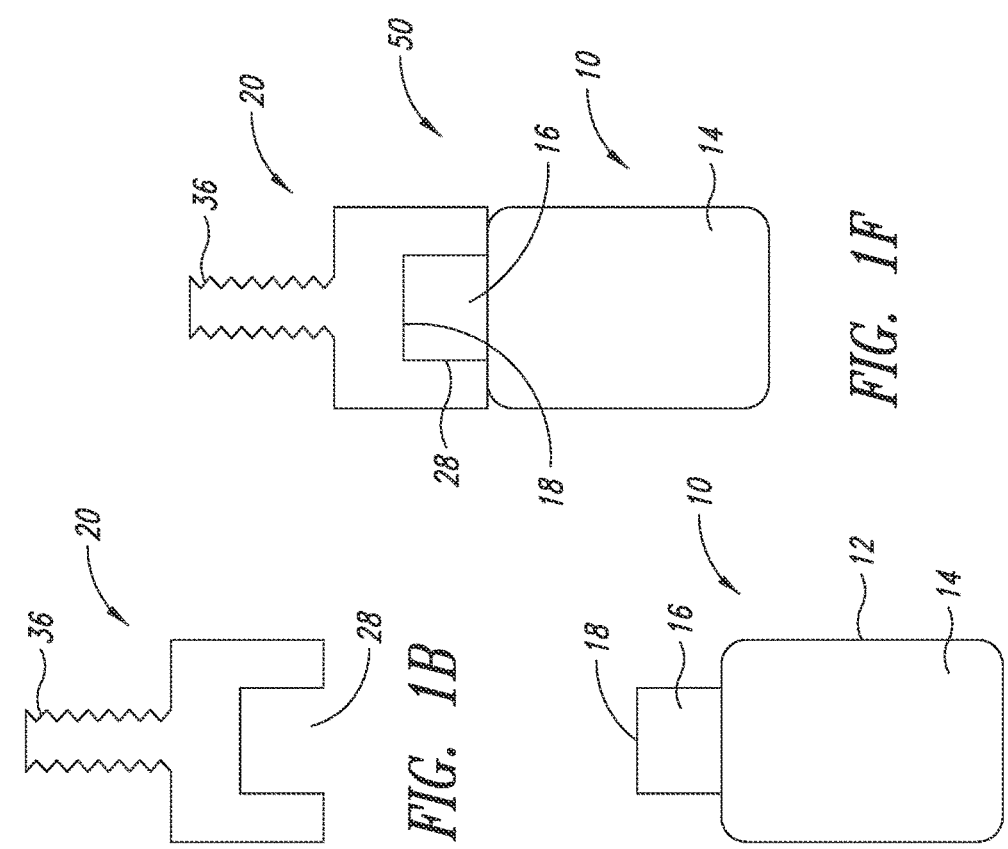

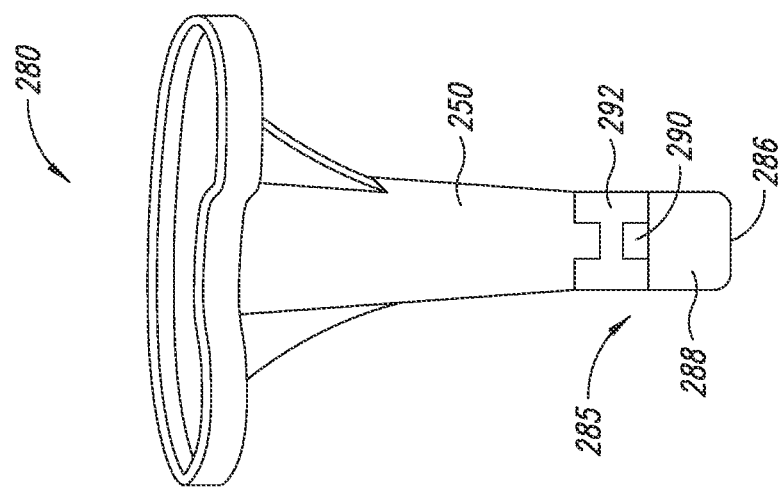
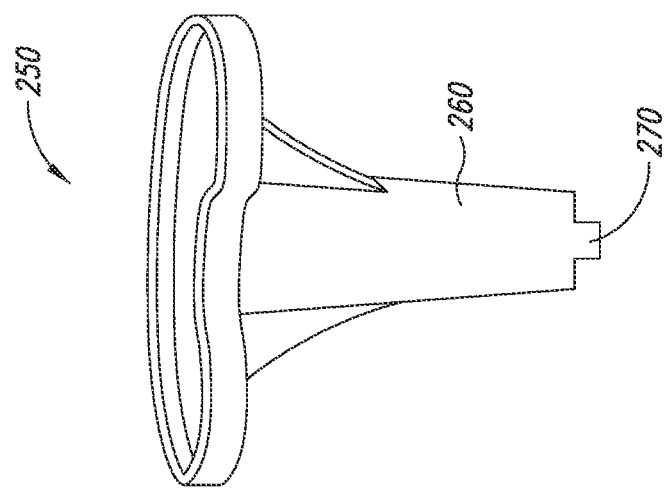
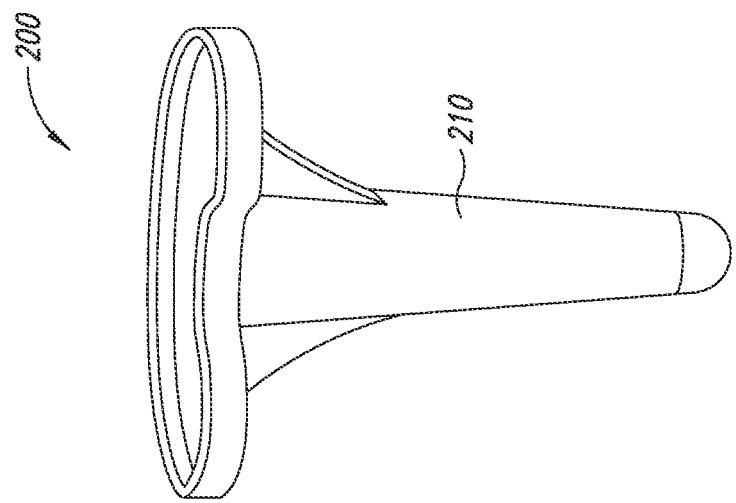
FIG. 2A (Prior Art)
FIG. 2B
FIG. 2C

MULTI-PIECE IMPLANTABLE JOINT PROSTHESIS

INCORPORATION BY REFERENCE TO ANY PRIORITY APPLICATIONS

Any and all applications for which a foreign or domestic priority claim is identified in the Application Data Sheet as filed with the present application are hereby incorporated by reference.

BACKGROUND

Field

The present disclosure relates generally to an implantable medical device and components thereof, including methods of making and using the device and components, and more specifically to alert implants with implantable reporting processors that may, e.g., monitor host activity, store measurements and output data.

Description of the Related Art

Medical devices and implants have become commonplace in modern medicine. Typically, medical devices and implants are manufactured to replace, support, or enhance an anatomical or biological structure. When the medical device is located on the surface of the patient, the device is readily viewable by the patient and the attending health care professional. However, when the medical device is designed to be implanted in a patient, i.e., is an implantable medical device or a medical implant, it is typically not readily viewable.

Examples of medical implants include orthopedic implants such as hip and knee prosthesis; spinal implants and hardware (spinal cages, screws, plates, pins, rods and artificial discs); intrauterine devices; orthopedic hardware used to repair fractures and soft tissue injuries (casts, braces, tensor bandages, plates, screws, pins and plates); cochlear implants; aesthetic implants (breast implants, fillers); and dental implants.

Unfortunately, various complications may arise during insertion of the medical implant (whether it is an open surgical procedure or a minimally invasive procedure). For example, a surgeon may wish to confirm correct anatomical alignment and placement of the implant within surrounding tissues and structures. This can however be difficult to do during the procedure itself, making corrective adjustments difficult.

In addition, a patient may experience a number of complications post-procedure. Such complications include neurological symptoms, pain, malfunction (blockage, loosening, etc.) and/or wear of the implant, movement or breakage of the implant, inflammation and/or infection. While some of these problems can be addressed with pharmaceutical products and/or further surgery, they are difficult to predict and prevent; often early identification of complications and side effects is difficult or impossible.

The present disclosure discloses novel medical devices, including medical implants, which can overcome difficulties and limitations found with previous medical devices and implants, methods for constructing and monitoring these novel medical devices and implants, and further provides other related advantages.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

In brief, in one aspect, the present disclosure provides a multi-piece medical device that may be implanted into a subject to provide structural support to the subject. In one embodiment, the multi-piece medical device is a prosthesis, i.e., an artificial body part, such as a leg, a heart, or a breast implant. In one embodiment the multi-piece medical device is a joint prosthesis, such as a replacement for all or part of a joint in the body of a subject.

In one aspect, the multi-piece medical device of the present disclosure comprises two pieces that are jointed together to form the implanted medical device. In one aspect, the multi-piece medical device of the present disclosure consists of two pieces that are joined together to form the implanted medical device. One, and optionally only one, of the two pieces contains one or more electronic components that may be located entirely within the body of the piece.

In one aspect, the multi-piece medical device of the present disclosure comprises at least two pieces that are joined together through an adapter. One, and optionally only one, of the two pieces contains one or more electronic components that may be located entirely within the body of the piece. Each of the two pieces includes a coupler, where the coupler is a mechanical feature of a piece that is utilized to couple the piece to the adapter. In one embodiment, the only function of a coupler is to allow coupling of the piece to an adapter. Each coupler has a coupling configuration, where a coupling configuration refers to the shape and/or to the size of the coupler. Two couplers couple by way of a coupling mechanism, and have complementary coupling configurations.

In one aspect, the multi-piece medical device of the present disclosure may be described, in whole or in part, as comprising [piece 1-$1^{st}$ coupler]-[$2^{nd}$ coupler-adapter-$3^{rd}$ coupler]-[$4^{th}$ coupler-piece 2]. Because a multi-piece medical device of the present disclosure may be assembled from multiple pieces (e.g., at least two pieces plus an adapter positioned between two of the at least two pieces) the medical device of the present disclosure may be referred to as a multi-piece medical device. In one aspect, the present disclosure provides a multi-piece implantable joint prosthesis.

In one embodiment, the combination of piece 1, adapter and piece 2 provides a fully functional implantable medical device. In one embodiment, each of piece 1, adapter and piece 2 contributes to the total surface area of the medical device, so that all of piece 1, adapter and piece 2 are necessarily present in order to provide a fully functional implantable medical device.

Thus, in one embodiment the present disclosure provides a multi-piece implantable joint prosthesis that includes an adapter to which at least two pieces are coupled, where the adapter has a coupler for coupling to a first piece and a different coupler for coupling to a second piece, where at least one piece, e.g., the first piece, may contain an electronic component such as a sensor that detects and measures movement of the prosthesis when the prosthesis is implanted in a patient, and can thus monitor the kinematic movement of the patient in real life situations, where the electronic component may also include a memory to store the data obtained by the sensor, and a communication interface to transmit the data to an external location where it may be analyzed, and a power source to provide power to the sensor, memory and communication interface.

In other aspects, the present disclosure provides pieces that may be coupled together via an adapter to provide some or all of a medical implant. In other aspects, the present disclosure provides an adapted piece, which refers to a portion of an implantable medical device that is coupled to an adapter, where the adapter includes an uncoupled coupler that may be used to couple the adapted piece to another piece of the implantable medical device so as to form a multi-piece medical device. The first piece may be referred to herein as the joint prosthesis component and the corresponding adapted piece may be referred to herein as an adapted joint prosthesis component. The second piece may be referred to as the precursor joint prosthesis. In one embodiment, the precursor joint prosthesis provides the majority of the surface area of the multi-piece implantable joint prosthesis, e.g., 60% or 70%, or 80%, or 90% or more than 90% of the surface area of the multi-piece implantable joint prothesis.

The present disclosure provides implantable medical devices that are multi-component and methods of forming and using these devices. The devices are particularly versatile in that one piece that contains electronic component(s) can be coupled to a wide variety of second pieces via an appropriately shaped and sized adapter, to provide a functioning sensor-containing implantable medical device.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter. The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIG. 1A is a schematic illustration of a prosthesis component of the present disclosure.

FIGS. 1B, 1C, 1D and 1E are each schematic illustrations of different adapters of the present disclosure.

FIG. 1F is a schematic illustration of the prosthesis component of FIG. 1A coupled to the adapter of FIG. 1B to provide an adapted prosthesis component.

FIG. 2A is a perspective view of a tibial component of a knee prosthesis (prior art).

FIG. 2B is a perspective view of a portion of a multi-piece implantable joint prosthesis of the present disclosure, and more specifically a truncated tibial component of a knee prosthesis.

FIG. 2C is a perspective view of a multi-piece implantable joint prosthesis of the present disclosure, and more specifically an implantable tibial component of a knee prosthesis formed from a truncated tibial component coupled to an adapted prosthesis component.

DETAILED DESCRIPTION

Figures 3A, 3B, 3C:
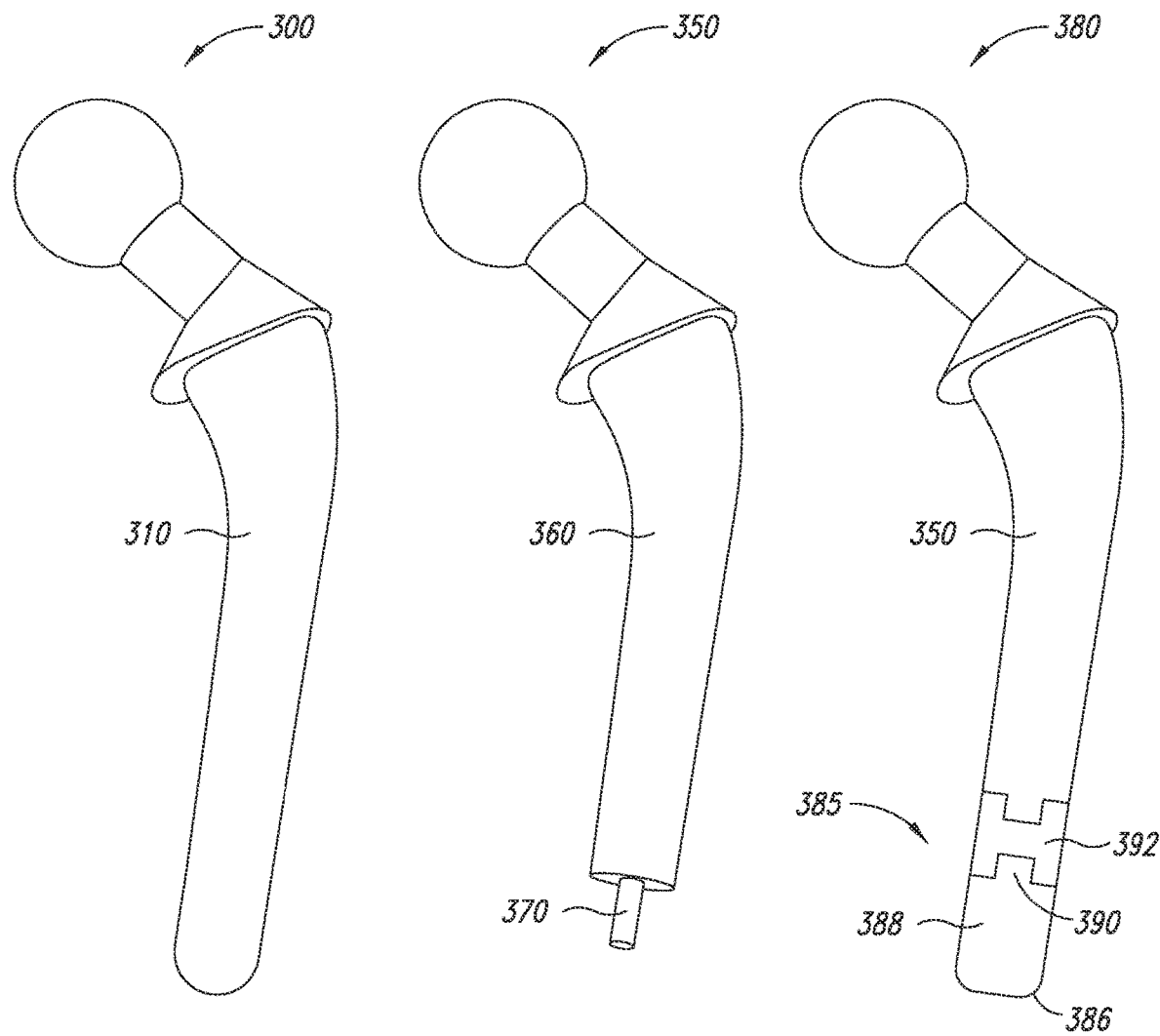
FIG. 3A is a perspective view of a femoral component of a hip prosthesis (prior art).
FIG. 3B is a perspective view of a portion of a multi-piece medical device of the present disclosure, and more specifically a truncated femoral component of a hip prosthesis.
FIG. 3C is a perspective view of a multi-piece implantable joint prosthesis of the present disclosure, and more specifically a multi-piece implantable femoral component of a hip prosthesis formed from a truncated femoral component coupled to an adapted prosthesis component.

The present disclosure may be understood more readily by reference to the following detailed description of preferred embodiments. In reading this detailed description, and unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin exempli gratia and is used herein to indicate a non-limiting example. Thus, the abbreviation "e.g." is synonymous with the term "for example."

Definitions

Prior to setting forth this disclosure in more detail, it may be helpful to an understanding thereof to provide definitions of certain terms to be used herein.

Adapted prosthesis component and adapted joint prosthesis component refer to a prosthesis component to which has been added an adapter. When the prosthesis is a joint prosthesis then the adapted prosthesis may be referred to as an adapted joint prosthesis component. An adapted joint prosthesis component may be coupled to a joint prosthesis precursor to provide a multi-piece implantable joint prosthesis of the present disclosure.

Adapter refers to a structural piece having two couplers, which may be referred to as a second coupler and a third coupler. It is noted that the term first coupler is reserved for a coupler that is part of the first piece (which will be a prosthesis component, e.g., a joint prosthesis component), while the term fourth coupler is reserved for a coupler that is part of the second piece (which will be the precursor prosthesis, e.g., a precursor joint prosthesis). Each of the couplers of the adapter has a coupling configuration, e.g., threads, that may interact via a coupling mechanism, e.g., by screwing two pieces together, with a coupler on a first or second piece. In this way, a first piece and a second piece may each independently couple to the adapter to secure the first and second pieces indirectly together (via the adapter).

In one embodiment, the adapter is a solid structure in that it does not contain an internal channel through which electronics, e.g., a wire, may be run in order to allow an electronic connection between the two pieces being coupled together by the adapter, e.g., the first piece and the second piece. Thus, in this embodiment, the two couplers of the adapter are not in communication with one another via any opening or channel or cavity that is located internal to the adapter.

Coupler refers to a structural feature that is part of a piece, or part of an adapter, where the coupler has the primary function of being useful to secure the coupler-containing piece to the coupler-containing adapter. An example of a coupler is a threaded post, where a complementary coupler (complementary to the threaded post) is a threaded hole, where the threaded post may be screwed securely into the threaded hole.

Coupled refers to the joining together of a piece and an adapter by way of complementary couplers on the piece and adapter. In one aspect, the piece and adapter are securely coupled, in that they will not decouple under normal in vivo conditions when implanted in a subject.

Coupling configuration refers to a physical shape and/or size of a coupler, where the shape is complementary to the shape and size of another coupler, so that the two complementary couplers may be coupled together. Examples of a coupling configuration include, without limitation, a Morris taper, a threaded rod, a polygonal rod, a cylindrical rod, and a Bayonet Neill-Concelman (BNC).

Coupling mechanism refers to the process by which two couplers are coupled together. Examples of coupling mechanisms include, without limitation, welding, threaded coupling (screwing two pieces together), mechanical coupling such as interference fit (a.k.a. press fit, friction fit) and bolting, and adhesive bonding.

Electronic component refers to one or more electronic components selected from, for example, a sensor, a memory, a power supply, and a communication interface. The electronic component may include one or more of a signal portal, an electronics assembly, and a power source. The signal portal functions to receive and transmit wireless signals, and may contain, for example, an antenna for transmitting the wireless signals. The electronics assembly may include a circuit assembly which may comprise, e.g., a PC board and electrical components formed on one or more integrated circuits (ICs) or chips, such as a radio transmitter chip, a real-time clock chip, one or more sensor components, e.g., an Inertial Measurement Unit (IMU) chip, temperature sensor, pressure sensor, pedometer, a memory chip, and the like. In addition, the electronics assembly may include a header assembly which provides a communication interface between the circuit assembly and the signal portal (e.g., antenna). The power source provides the energy needed to operate the electronic components, and may be, for example, a battery. The components may include one or more sensors, such as gyroscopes, accelerometers, pedometers, and temperature and pressure sensors, where in one embodiment the sensor is located on a PC board. In one embodiment, the electronic component includes a space-efficient, printed-circuit assembly (PCA). The implantable reporting processor may include a plurality of transmitting antennae structured in different configurations. As such, an embodiment of the present invention is directed to a plurality of enhanced space-efficient and power-efficient antenna configurations. Electronic circuitry is disposed in a piece of the present disclosure, such as a first piece of a multi-piece implantable joint prosthesis, and is configured to provide, to a destination outside of a patient's body, information related to the prosthesis. The electronic components including the power supply may be disposed within a housing.

Implantable prosthesis or implantable joint prosthesis and multi-part implantable joint prosthesis refer to a prosthesis that may be implanted into a subject and upon implantation will provide all the physical support and structural benefits expected of a fully functional implanted prosthesis. When the implantable prosthesis is implanted to replace some or all of joint of the subject, then the implantable prosthesis may be referred to as an implantable joint prosthesis, in which case the prosthesis provides all the physical support and structural benefits expected to a fully functional implanted prosthesis as well as some or all the freedom of movement (kinematic properties) that an implanted joint prosthesis is expected to provide in order to function as a fully functional implanted joint prosthesis. An example of an implantable joint prosthesis is a tibial component of a knee prosthesis. Tibial components are well known in the art of medical implants and are utilized to provide certain physical support and structural benefits that would ordinarily be provided by the healthy form of the tibia bone that is being replaced, in part, by the tibial component. The prosthetic tibial component is of a size and shape, and is made of a sufficiently sturdy and durable material, that it can replace a portion of the tibia of a subject, and thereupon provide the structural and support benefits formerly provided by the portion of the tibial that the prosthesis has replaced, had that portion been in a healthy state and not needed to be replaced. The implantable joint prosthesis of the present disclosure may have the overall appearance and the physical and kinematic properties of a prior art implantable joint prosthesis, however, an implantable joint prosthesis of the present disclosure will, in one aspect, include an adapter and will thus be a multi-piece implantable joint prosthesis. In one embodiment, an implantable joint prosthesis of the present disclosure is formed from the coupling together of a joint prosthesis component, via an adapter, to a precursor joint prosthesis, or comprises, or consists essentially of, or consists of, a joint prosthesis component, a precursor joint prosthesis and an adapter located therebetween. As described elsewhere herein, in one aspect a multi-piece joint prosthesis of the present disclosure does not include an adapter, but instead comprises, or consists essentially of, or consists of, two pieces: the piece containing the electronics and the precursor joint prosthesis.

Precursor prosthesis or precursor joint prosthesis refers to a piece to which the adapted prosthesis component may be coupled in order to provide an implantable prosthesis. When the implantable prosthesis is an implantable joint prosthesis, then the precursor prosthesis may be referred to as a precursor joint prosthesis. In one embodiment, the precursor joint prosthesis may be a shortened form of an implantable joint prosthesis, e.g., a tibial component of a knee prosthesis having a shortened stem or a femoral component of a hip prosthesis having a shortened stem. In the case where the precursor joint prosthesis is a truncated form of an implantable joint prosthesis, the addition of the adapted joint prosthesis component to the truncated joint prosthesis may provide a multi-piece implantable joint prosthesis of the present disclosure.

Prosthesis component or joint prosthetic component refers to a body surrounded at least partially by a housing, where the body optionally includes one or more electronic components selected from, for example, a sensor, a memory, a power supply, and a communication interface. When the prosthesis is a joint prosthesis, the prosthesis component may be referred to as a joint prosthesis component, and the multi-part implantable prosthesis may be referred to as the multi-part implantable joint prosthesis. In one aspect, a prosthesis component of the present disclosure is a part of a multi-piece implantable prosthesis of the present disclosure. A joint prosthesis component of the present disclosure is a part of a multi-piece implantable joint prosthesis of the present disclosure, where the joint prosthesis component provides sensing functionality. In one aspect, the joint prosthesis component provides a necessary structural benefit to the multi-piece implantable joint prosthesis.

Embodiments of the present disclosure will now be described with reference to associated Figures.

FIG. 1A is a schematic illustration of a piece, and more specifically a prosthesis component of the present disclosure. In FIG. 1A, the prosthesis component 10 comprises a housing 12 and a body 14 that is contained within the housing 12. The body 14 may contain an electronic component, such as one or more of a sensor, a power supply, a memory and a communication interface (not shown). The prosthesis component 10 also comprises a coupler 16 having a first coupling configuration 18. The coupler 16 may be referred to as the first coupler. The coupler 16 serves to provide an attachment point whereby the prosthesis component may be coupled in a secure manner to an adapter. In FIG. 1A, the coupler 16 is illustrated as an extension from the body 14, i.e., as a male part of a coupled unit, and has flat surfaces. However, in embodiments, the coupling configuration may be an extension from the body 14 where the coupler does not have flat surfaces, or in embodiments the coupling configuration of the coupler may be a recess instead of an extension, where in embodiments, the recess may or may not have flat surfaces.

FIG. 1B, FIG. 1C, FIG. 1D and FIG. 1E illustrate exemplary adapters 20, 22, 24 and 26, respectively, of the present disclosure. Each adapter of the present disclosure comprises two distinct couplers, a second coupler having a second coupling configuration and a third coupler having a coupling configuration, where a first coupling mechanism couples the first coupler having a first coupling configuration of the joint prosthesis component to the second coupler having a second coupling configuration of the adapter to provide the adapted joint prosthesis component. For example, each of the adapters 20, 22, 24 and 26 comprises a second coupler 28, 30, 32 and 34, respectively, and a third coupler 36, 38, 40 and 42, respectively. The third coupler is designed to couple the adapter to a precursor joint prosthesis, where the precursor joint prosthesis comprises a fourth coupler having a fourth coupling configuration that is complementary to the third coupling configuration of the third coupler present as part of the adapter.

Thus, an adapter of the present disclosure has two couplers which are referred to for convenience as the second coupler and the third coupler (the first coupler being a feature of the joint prosthesis component). The first and second couplers couple to one another via a first coupling mechanism. The third and fourth couplers couple to one another via a second coupling mechanism. The first and second coupling configurations are therefore complementary to one another. Likewise, the third and fourth coupling configurations are complementary to one another. In one aspect, a coupler is selected from a Morris taper, a threaded rod, a polygonal rod, a cylindrical rod, a Bayonet Neill-Concelman (BNC), and a complement thereof.

FIGS. 1B, 1C, 1D and 1E illustrate exemplary adapters 20, 22, 24 and 26, respectively, of the present disclosure. The adapter 20 of FIG. 1B has a second coupler 28 that is a female part having straight sides, and a third coupler 36 that is a male part having threaded sides. The adapter 22 of FIG. 1C has a second coupler 30 that is a male part having straight sides, and a third coupler 38 that is a female part having threaded sides. The adapter 24 of FIG. 1D has a second coupler 32 that is a female part having straight sides, and a third coupler 40 that is a female part having straight sides, where the size of the second coupler is smaller than the size of the third coupler. The adapter 26 of FIG. 1E has a second coupler 34 that is a male part with straight sides, and a third coupler 42 that is a male part having threaded sides.

FIG. 1F is a schematic illustration of the prosthesis component 10 of FIG. 1A coupled to the adapter 20 of FIG. 1B to provide an adapted prosthesis component 50. In FIG. 1F, a first coupling mechanism couples the first coupler 18 of the joint prosthesis component 10 to the second coupler 28 of the adapter 20 to provide the adapted prosthesis component 50, where a second coupling mechanism can couple the third coupler 36 of the adapter 20 to a fourth coupler (not shown) of, in one embodiment, a precursor joint prosthesis (not shown) to provide a multi-piece implantable joint prosthesis (not shown).

Thus, in one aspect, the present disclosure provides an adapted joint prosthesis component for coupling to a precursor joint prosthesis to provide a multi-piece implantable joint prosthesis. The adapted joint prosthesis component comprises a joint prosthesis component comprising a housing, a body enclosed by the housing, and a first coupler. The body contains one or more electronic components, where exemplary electronic components may be selected from a sensor, a memory, a power supply, and a communication interface. The first coupler has a first coupling configuration. The adapted joint prosthesis component also comprises an adapter, the adapter comprising a second coupler having a second coupling configuration, and a third coupler having a third coupling configuration, where a first coupling mechanism couples the first coupling configuration of the first coupler of the joint prosthesis component to the second coupling configuration of the second coupler of the adapter to provide the adapted joint prosthesis component. The referenced precursor joint prosthesis comprises a fourth coupler having a fourth coupling configuration, where a second coupling mechanism can couple the third coupling configuration of the adapter to the fourth coupling configuration of the precursor joint prosthesis to provide the multi-piece implantable joint prosthesis.

In one aspect, the present disclosure provides a multi-piece implantable prosthesis that is formed from an adapted prosthesis component and a precursor prosthesis, where neither of the adapted prosthesis component nor the precursor prosthesis is, by itself, a functional implantable joint prosthesis. Only when the two pieces are coupled together, i.e., only after the adapted prosthesis component and the precursor prosthesis are coupled together, does a functioning implantable prosthesis result. This situation is illustrated with reference to some of the following Figures, where the prosthesis used in the Figures is a joint prosthesis.

FIG. 2A is a perspective view of a tibial component of a knee prosthesis 200 (prior art). The tibial component 200 includes a tibial stem 210. The prosthesis 200 provides all the structural features needed for an effective implanted joint prosthesis.

FIG. 2B is a perspective view of a precursor joint prosthesis 250 of the present disclosure, and more specifically a truncated tibial component of a knee prosthesis. The prosthesis 250 includes a truncated tibial stem 260 which is shorter than the tibial stem 210 of the tibial component 200 of FIG. 2A. Thus, in FIG. 2B, the truncated tibial component does not provide the complete functional properties of an implantable tibial component because the tibial stem 260 is insufficiently long to provide the desired stability afforded by the longer stem 210. In addition to having a shortened tibial stem, the truncated joint prosthesis has a fourth coupler 270 with a fourth coupling configuration which can be coupled to a third coupler of an adapted joint prosthesis component having a complementary third coupling configuration as described elsewhere herein. In FIG. 2B, the coupler 270 comprises a fourth coupler having a fourth coupling configuration which, as illustrated, is a male component with straight sides, however as made clear herein, a male component with straight sides is not limiting of the fourth coupling configurations of the present disclosure.

FIG. 2C is a perspective view of a multi-piece implantable joint prosthesis 280 of the present disclosure, and more specifically a multi-piece implantable tibial component of a knee prosthesis 280 that is assembled from a truncated tibial component 250 as illustrated in FIG. 2B coupled to an adapted joint prosthesis component 285 having a joint prosthesis component as illustrated in FIG. 1A and an adapter as illustrated in FIG. 1D. The adapted joint prosthesis component 285 comprises a housing 286 and a body 288 that is contained within the housing 286. The body 288 may comprise an electronic component such as one or more of a sensor, a power supply, a memory and a communication interface (not shown), which are exemplary electronic components. The adapted joint prosthesis component 285 also comprises a coupler 290 that is coupled to an adapter 292, where the adapter is likewise coupled to the truncated tibial component 250. The combination of the adapted joint prosthesis component 285 and the truncated joint prosthesis 250 provides a multi-piece implantable joint prosthesis having the structural functionality of the tibial component of a knee prosthesis 200 of FIG. 2A, although also having electronic functionality via the features in the body of the adapted joint prosthesis component.

FIG. 3A is a perspective view of a femoral component of a hip prosthesis 300 (prior art). The femoral component 300 includes a femoral stem 310. The prosthesis 300 provides all the structural features needed for an effective implanted joint prosthesis.

FIG. 3B is a perspective view of a precursor joint prosthesis 350 of the present disclosure, and more specifically a truncated femoral component of a hip prosthesis. The truncated joint prosthesis 350 includes a truncated femoral stem 360 which is shorter than the femoral stem 310 of the femoral component 300 of FIG. 3A. Thus, in FIG. 3B, the truncated femoral component does not provide the complete functional properties of an implantable femoral component because the femoral stem 360 is insufficiently long to provide the desired stability afforded by the longer stem 310. In addition to having a shortened femoral stem, the truncated joint prosthesis comprises a fourth coupler 370.

In one aspect (not shown), the fourth coupler has a fourth coupling configuration which is complementary to a piece having electronic components as described herein. In this aspect, the piece having electronic components is joined directly to the truncated femoral stem 360, to provide the implantable medical device. In this aspect, no adapter is positioned between the piece with electronic components and the truncated femoral stem 360. In FIG. 3B, the fourth coupler 370 is illustrated as a male component with straight sides, however as made clear herein, a male component with straight sides is not limiting of the fourth coupling configurations of the present disclosure.

In one aspect (see, e.g., FIG. 3C below), the truncated femoral stem 360 may be described as having a fourth coupling configuration, where the fourth coupling configuration is complementary to a third coupling configuration of an adapted joint prosthesis component described elsewhere herein. In FIG. 3B, the fourth coupler 370 is illustrated as a male component with straight sides, however as made clear herein, a male component with straight sides is not limiting of the fourth coupling configurations of the present disclosure.

FIG. 3C is a perspective view of a multi-piece implantable joint prosthesis 380 of the present disclosure, and more specifically a multi-piece implantable femoral component of a hip prosthesis 380 that is formed from a truncated femoral component 350 coupled to an adapted joint prosthesis component 385. The adapted joint prosthesis component 385 comprises a housing 386 and a body 388 that is contained within the housing 386. The body 388 may comprise an electronic component, for example, one or more of a sensor, a power supply, a memory and a communication interface (not shown) as exemplary electronic components. The adapted joint prosthesis component 385 also comprises a coupler 390 that is coupled to an adapter 392 such as illustrated in FIG. 1D, where the adapter 392 is likewise coupled to the truncated femoral component 350. The combination of the adapted joint prosthesis component 385 and the truncated joint prosthesis 350 provides a multi-part implantable joint prosthesis 380 having the structural functionality of the tibial component of a knee prosthesis 300 of FIG. 3A, although the multi-part implantable joint prosthesis 380 has enhanced electronic functionality due to the features in the body of the adapted joint prosthesis component which are absent in the prosthesis of FIG. 3A.

Figure 4A:
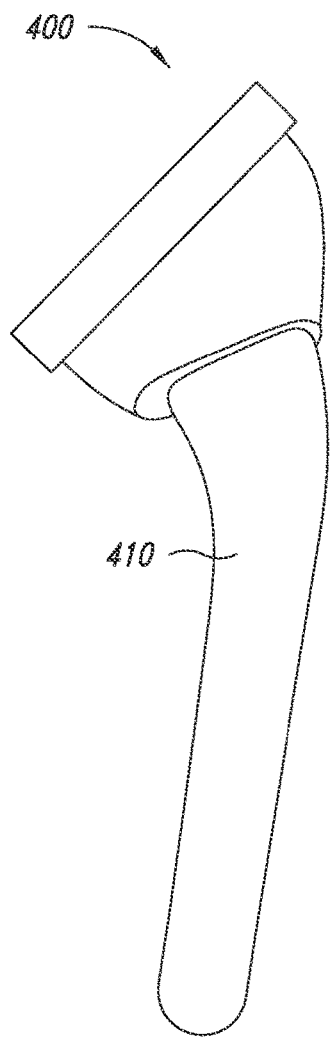
FIG. 4A is a perspective view of a humeral component of a shoulder prosthesis (prior art).

FIG. 4A is a perspective view of a humeral component of a shoulder prosthesis 400 (prior art). The femoral component 400 includes a humeral stem 410. The prosthesis 400 provides all the structural features needed for an effective implanted joint prosthesis.

Figure 4B:
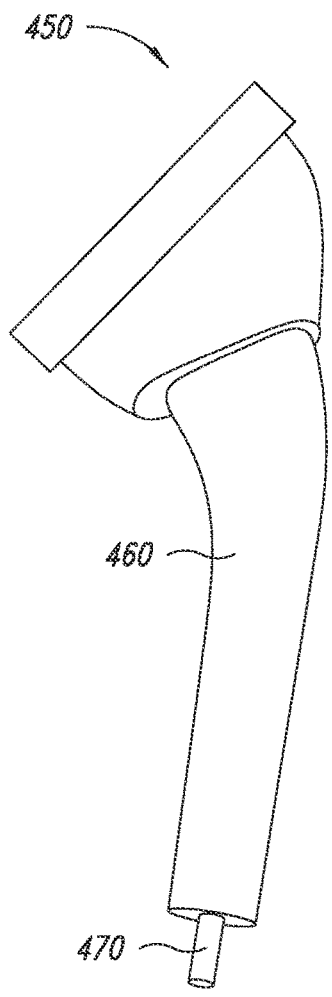
FIG. 4B is a perspective view of a portion of a multi-piece medical device of the present disclosure, and more specifically a truncated humeral component of a shoulder prosthesis.

FIG. 4B is a perspective view of a precursor joint prosthesis 450 of the present disclosure, and more specifically a truncated humeral component of a shoulder prosthesis. The precursor joint prosthesis 450 includes a truncated humeral stem 460 which is shorter than the humeral stem 450 of the femoral component 400 of FIG. 4A. Thus, in FIG. 4B, the truncated humeral component does not provide the complete functional properties of an implantable humeral component because the humeral stem 460 is insufficiently long to provide the desired length afforded by the longer stem 410. In addition to having a shortened humeral stem, the precursor joint prosthesis 450 has a fourth coupler 470 which may be characterized by a fourth coupling configuration.

In one aspect (not shown), the fourth coupler has a fourth coupling configuration which is complementary to a piece having electronic components as described herein. In this aspect, the piece having electronic components is joined directly to the truncated humeral stem 460, to provide the implantable medical device. In this aspect, no adapter is positioned between the piece with electronic components and the truncated femoral stem 460. In FIG. 4B, the fourth coupler 470 is illustrated as a male component with straight sides, however as made clear herein, a male component with straight sides is not limiting of the fourth coupling configurations of the present disclosure.

In one aspect (e.g., FIG. 4C below), the truncated humeral stem 460 may be described as having a fourth coupling configuration, where the fourth coupling configuration is complementary to a third coupling configuration of an adapted joint prosthesis component described elsewhere herein. In FIG. 4B, the fourth coupler 470 is illustrated as a male component with straight sides, however as made clear herein, a male component with straight sides is not limiting of the fourth coupling configurations of the present disclosure.

Figure 4C:
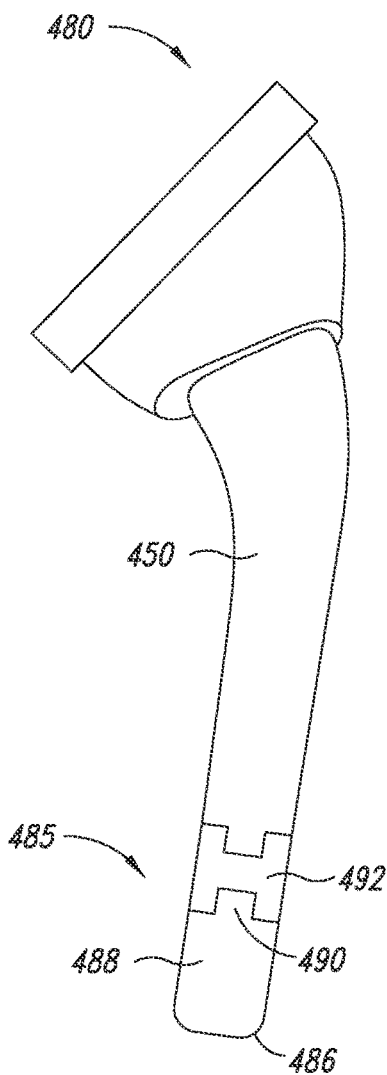
FIG. 4C is a perspective view of a multi-piece implantable joint prosthesis of the present disclosure, and more specifically a multi-piece implantable humeral component of a shoulder prosthesis formed from a truncated humeral component coupled to an adapted prosthesis component.

FIG. 4C is a perspective view of a multi-piece implantable joint prosthesis 480 of the present disclosure, and more specifically a multi-piece implantable humeral component of a shoulder prosthesis 480 that is formed from a precursor joint prosthesis 450 (see FIG. 4B) coupled to an adapted joint prosthesis component 485. The adapted joint prosthesis component 485 comprises a housing 486 and a body 488 that is contained within the housing 486. The body 488 may comprise an electronic component, e.g., one or more of a sensor, a power supply, a memory and a communication interface (not shown) as exemplary electronic components. The adapted joint prosthesis component 485 also comprises a coupler 490 that is coupled to an adapter 492 such as illustrated in FIG. 1D, where the adapter 492 is likewise coupled to the precursor joint (humeral) component 450. The combination of the adapted joint prosthesis component 485 and the precursor joint prosthesis 450 provides an implantable joint prosthesis 480 having the structural functionality of the humeral component of a shoulder prosthesis 400 of FIG. 4A, although the prosthesis 400 lacks the electronic functionality provided by the adapted joint prosthesis component.

Figure 5A:
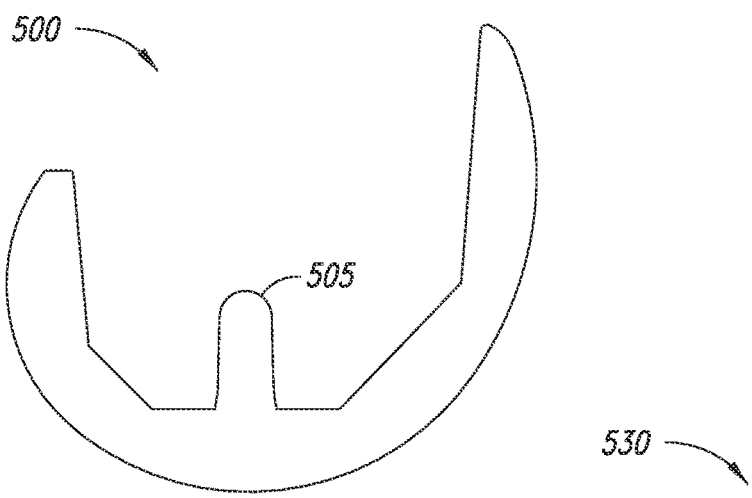
FIG. 5A is a perspective view of a femoral component of a knee prosthesis (prior art).

FIG. 5A is a perspective view of a femoral component 500 of a knee prosthesis (prior art). The femoral component 500 includes a post 505. The prosthesis 500 provides all the structural features needed for an effective implanted joint prosthesis.

Figure 5B:
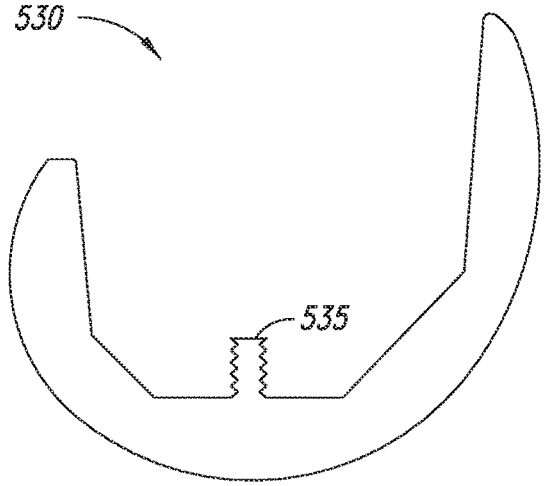
FIG. 5B is a perspective view of a portion of a multi-piece joint prosthesis of the present disclosure, and more specifically a truncated femoral component of a knee prosthesis.

FIG. 5B is a perspective view of a precursor joint prosthesis 530 of the present disclosure, and more specifically a modification of the femoral component of a knee prosthesis as shown in FIG. 5A. The precursor joint prosthesis 530 includes a threaded post 535 in lieu of the smooth post 505 that is present in the traditional femoral component 500 of FIG. 5A. The incorporation of threads as part of the post of a femoral component provides a fourth coupler having a fourth coupling configuration to a precursor joint prosthesis.

In one aspect (not shown), this fourth coupling configuration is complementary to a piece having electronic components as described herein. In this aspect, the piece having electronic components is joined directly to the truncated precursor joint prosthesis 530, to provide the implantable medical device. In this aspect, no adapter is positioned between the piece with electronic components and the precursor joint prosthesis 530. In FIG. 5B, the fourth coupler 535 is illustrated as a threaded post, however as made clear herein, a male component with the form of a threaded post is not limiting of the fourth coupling configurations of the present disclosure.

In one aspect, this fourth coupling configuration may be utilized in a second coupling mechanism to couple the precursor joint prosthesis 530 to an adapted joint prosthesis as described elsewhere herein, and more specifically the second coupling mechanism may couple the fourth coupler of the precursor joint prosthesis to the third coupler of an adapted joint prosthesis (not shown in FIG. 5B). Although the fourth coupler is illustrated in FIG. 5B as having threads on a post 535, the present disclosure is not limited to the use of threads to provide a coupling configuration, nor a post as a location to place the fourth coupling configuration.

Figure 5C:
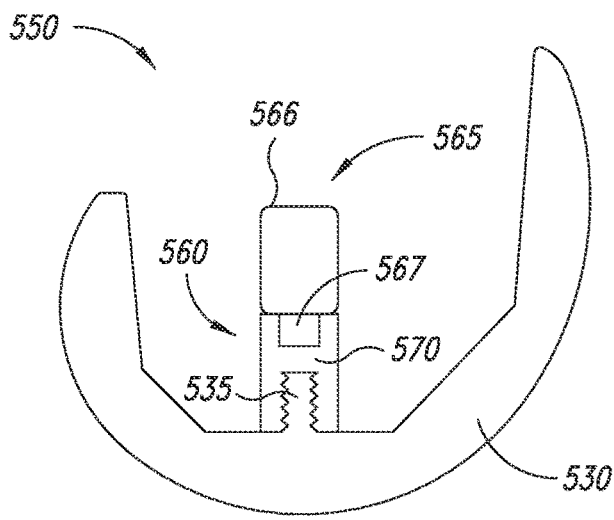
FIG. 5C is a perspective view of a multi-piece implantable joint prosthesis of the present disclosure, and more specifically a multi-piece implantable femoral component of a knee prosthesis formed from a truncated femoral component coupled to an adapted prosthesis component.

FIG. 5C is a perspective view of a multi-piece implantable joint prosthesis 550 of the present disclosure, and more specifically an implantable femoral component of a knee prosthesis formed from a precursor joint (femoral) component 530 coupled to an adapted joint prosthesis component 560. The adapted joint prosthesis component 560 includes a joint prosthesis component 565 coupled to an adapter 570, where the joint prosthesis component 565 comprises a housing 566, where the housing encloses an electronic component, e.g., one or more of a sensor, a power supply, a memory and a communication interface (not shown), and where the joint prosthesis component also comprises a coupler 567, and the housing 566 and the coupler 567 together provide the exterior surface of the joint prosthesis component 565, where the coupler 567 comprises a first coupling configuration, where a first coupling mechanism couples the first coupling configuration of the coupler to a second coupling configuration of the adapter to provide the adapted joint prosthesis component.

Figure 6A:
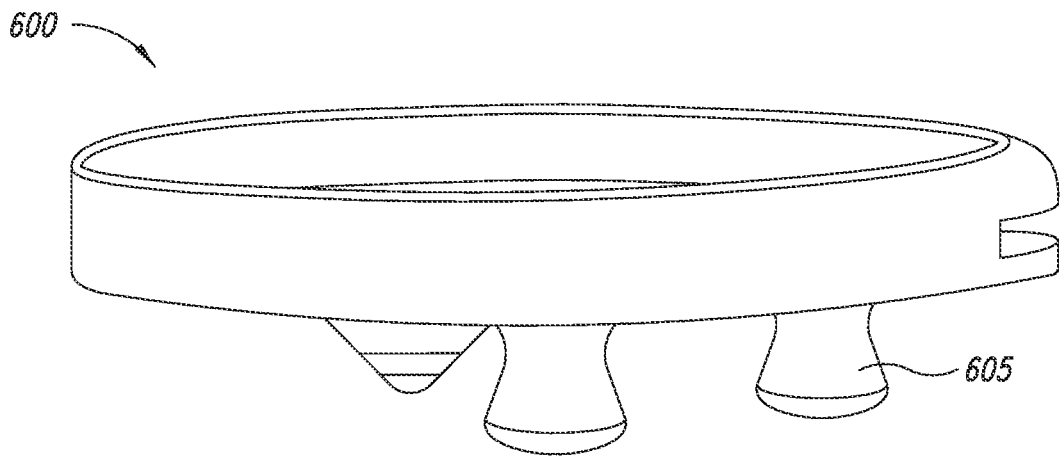
FIG. 6A is a perspective view of a partial tibial component of a knee prosthesis (prior art).

FIG. 6A is a perspective view of a partial tibial component of a knee prosthesis 600 (prior art). The tibial component 600 includes a post 605. The prosthesis 600 provides all the structural features needed for an effective implanted joint prosthesis.

Figure 6B:
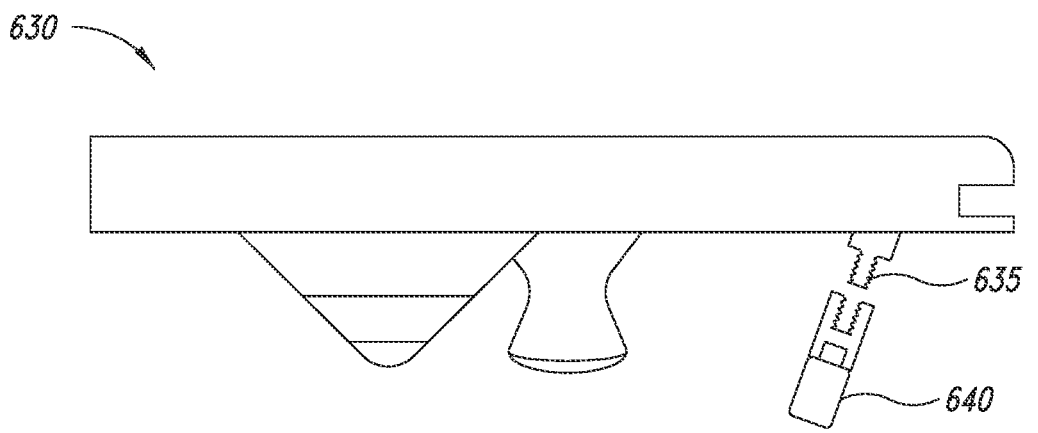
FIG. 6B is a perspective view of a portion of a multi-piece joint prosthesis of the present disclosure, and more specifically a truncated partial tibial component of a knee prosthesis.

FIG. 6B is a perspective view of a precursor joint prosthesis 630 of the present disclosure, and more specifically a precursor partial tibial component prosthesis. The precursor joint prosthesis 630 includes a threaded post 635 in lieu of the smooth bulbular post 605 that is present in the traditional partial tibial component 600 of FIG. 6A. The incorporation of threads as part of the post of a partial tibial component provides a fourth coupler that imparts a fourth coupling configuration to a precursor implantable joint prosthesis.

In one aspect (not shown in FIG. 6B), this fourth coupler has a fourth coupling configuration that is complementary to a piece having electronic components as described herein. In this aspect, the piece having electronic components is joined directly to the precursor joint prosthesis 630, to provide the implantable medical device. In this aspect, no adapter is positioned between the piece with electronic components and the precursor joint prosthesis 630. In FIG. 6B, the fourth coupler 635 is illustrated as a threaded post, however as made clear herein, a male component with the form of a threaded post is not limiting of the fourth coupling configurations of the present disclosure.

In one aspect, as shown in FIG. 6B, this fourth coupler may be utilized in a second coupling mechanism to couple the precursor joint prosthesis 630 to the adapted joint prosthesis 640 as described elsewhere herein, and more specifically the second coupling mechanism may couple the fourth coupler of the precursor joint prosthesis 630 to the third coupler of the adapted joint prosthesis 640. Although the fourth coupler 635 is illustrated in FIG. 6B as threads on a post, the present disclosure is not limited to the use of threads to provide a coupling configuration, nor a post as a location to place the fourth coupling configuration.

Figure 6C:
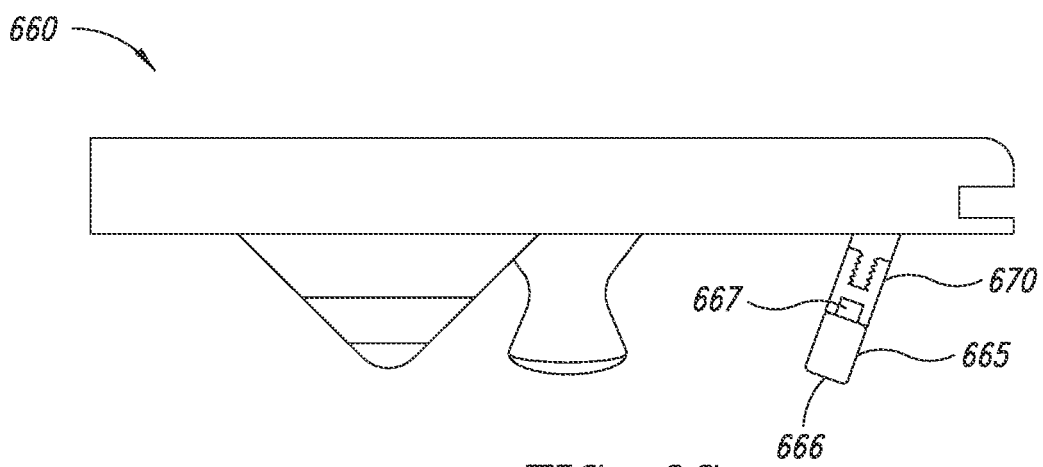
FIG. 6C is a perspective view of a multi-piece implantable joint prosthesis of the present disclosure, and more specifically a multi-piece implantable partial tibial component of a knee prosthesis formed from a truncated partial tibial component coupled to an adapted prosthesis component.

FIG. 6C is a perspective view of a multi-piece implantable joint prosthesis 660 of the present disclosure, and more specifically a multi-piece implantable partial tibial component of a knee prosthesis formed from a precursor partial tibial component 630 coupled to an adapted joint prosthesis component 640. The adapted joint prosthesis component 660 includes a joint prosthesis component 665 coupled to an adapter 670, where the joint prosthesis component 665 comprises a housing 666, where the housing 666 encloses a body comprising an electronic component, e.g., one or more of a sensor, a power supply, a memory and a communication interface (not shown), and where the joint prosthesis component 665 also comprises a coupler 667, and the housing 666 and the coupler 667 together provide the outer surface of the joint prosthesis component 665, where the coupler 667 has a first coupling configuration, where a first coupling mechanism couples the first coupler of the joint prosthesis component to the second coupler of the adapter to provide the adapted joint prosthesis component.

Figure 7A:
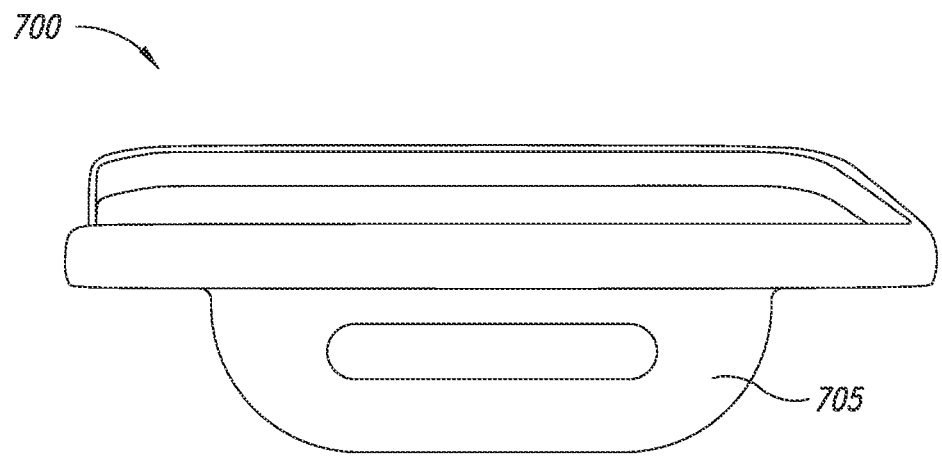
FIG. 7A is a perspective view of a partial tibial component of a knee prosthesis having a single keel (prior art).

FIG. 7A is a perspective view of a partial tibial component 700 of a knee prosthesis having a single keel 705 (prior art). The prosthesis 700 provides all the structural features needed for an effective implanted joint prosthesis.

Figure 7B:
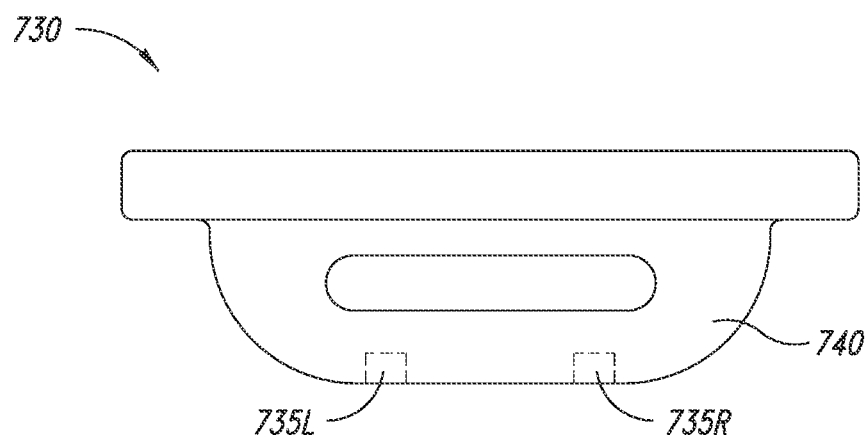
FIG. 7B is a perspective view of a modified partial tibial component of a knee prosthesis of the present disclosure.

FIG. 7B is a perspective view of a precursor joint prosthesis 730 of the present disclosure, which may be referred to as a modification of the partial tibial component 700 as shown in FIG. 7A. The precursor joint prosthesis 730 includes two recesses 735L and 735R in the keel 740 of the precursor joint prosthesis 730, where those recesses 735L and 735R are not present in the keel 705 of the partial tibial component 700. Either of the recesses 735L and 735R can be characterized as a fourth coupler. Although in FIG. 7B, the keel is shown as having two recesses, in other embodiments (not shown) the keel may have a single recess or may three recesses or more recesses. The fourth coupler has a fourth coupling configuration. As will be discussed below, these two recesses 735L and 735R function in concert to couple the precursor joint prosthesis 730 to an adapted prosthesis component.

In FIG. 7B, the recesses 735L and 735R are shown as structurally equivalent recesses, i.e., the recesses 735L and 735R are the same size and shape. More generally, the present disclosure provides that when a precursor joint prosthesis has more than one coupler, the two or more couplers may be equivalent or non-equivalent to one another. For example, one of the couplers may be a recess and another coupler may be an extension.

Figure 7C:
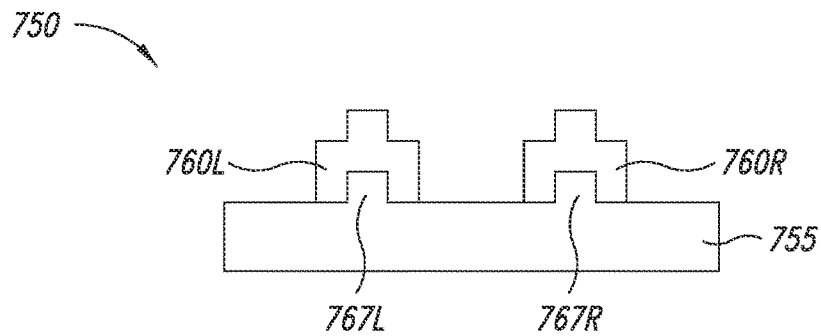
FIG. 7C is a schematic view of an adapted prosthesis component of the present disclosure.

FIG. 7C is a schematic view of an adapted joint prosthesis component 750 of the present disclosure, and more specifically an adapted partial knee prosthesis component. The adapted joint prosthesis component 750 includes a joint prosthesis component 755 coupled to two adapters, identified as 760R and 760L. Although structures 760R and 760L are shown as separate physical structures in FIG. 7C, in one embodiment of the present disclosure those separate physical structures may be joined together to provide a single structure adapter (not shown). However, in FIG. 7C, the joint prosthesis component 755 is coupled to two adapters, 760L and 760R.

In FIG. 7C, the joint prosthesis component 755 comprises a housing that encloses a body of the joint prosthesis component, where the body comprises an electronic component, such as one or more of a sensor, a power supply, a memory and a communication interface (not shown). The joint prosthesis component 755 further comprises a coupler 767L as well as an additional coupler 767R. An adapter 760L has a coupler than can couple to the coupler 767L so as to provide an adapted joint prosthesis component. An adapter 760R likewise has a coupler that can couple to the coupler 767R.

In one aspect (not shown), joint prosthesis component 755 may have one or more couplers that couple directly to the precursor joint prosthesis 730 shown in FIG. 7B. In this aspect, the configurations of couplers 735L and 735R of precursor 730 are complementary to the configurations of couplers 767L and 767R, respectively (as shown in FIGS. 7B and 7C). In this aspect, joint prosthesis component 755 contains electronic components as described herein. In this aspect, the piece having electronic components is joined directly to the precursor joint prosthesis 730, to provide the implantable medical device. In this aspect, no adapter is positioned between the piece with electronic components and the precursor joint prosthesis 730. In FIG. 7B, the fourth couplers 735L and 735R are illustrated as non-threaded indents, however as made clear herein, a female component with the form of a non-threaded indent is not limiting of the fourth coupling configurations of the present disclosure.

Figure 7D:
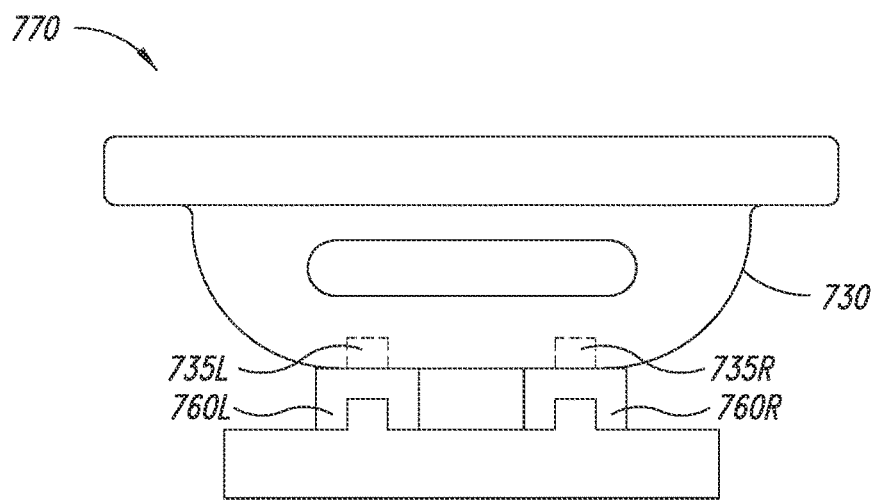
FIG. 7D is a schematic side view of an expanded implantable joint prosthesis of the present disclosure, and more specifically an expanded implantable partial tibial component of a knee prosthesis formed from the modified partial tibial component of FIG. 7B coupled to the adapted prosthesis component of FIG. 7C.

FIG. 7D is a schematic side view of a multi-piece implantable joint prosthesis of the present disclosure, and more specifically a multi-piece implantable partial tibial component 770 of a knee prosthesis formed from the precursor joint prosthesis 730 of FIG. 7B coupled to the adapted joint prosthesis component 750 of FIG. 7C. As shown in FIG. 7D, the third coupling configuration of the adapted joint prothesis 750 couples to a corresponding fourth coupling configuration of the precursor joint prosthesis 730 to couple these two components securely together.

Figure 7E:
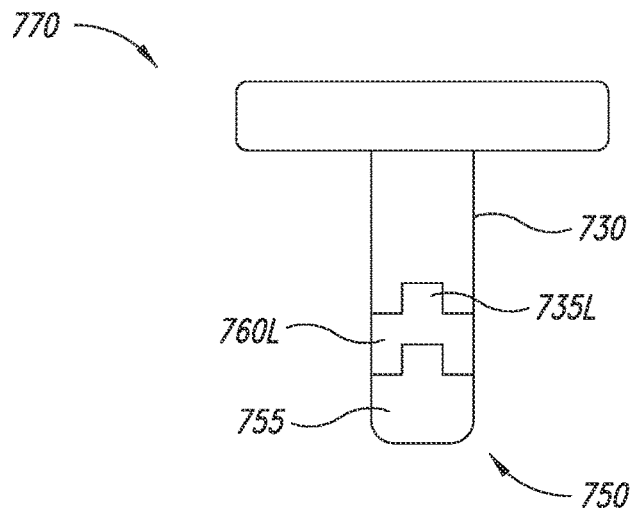
FIG. 7E is a schematic end view of the expanded implantable joint prosthesis of FIG. 7D, and more specifically an expanded implantable partial tibial component of a knee prosthesis formed from the modified partial tibial component of FIG. 7B coupled to the adapted prosthesis component of FIG. 7C.

FIG. 7E is a schematic end view of the multi-piece implantable joint prosthesis 770 of FIG. 7D of the present disclosure, and more specifically a multi-piece implantable partial tibial component of a knee prosthesis formed from the precursor joint prosthesis 730 of FIG. 7B coupled to the adapted joint prosthesis component 750 of FIG. 7C.

Thus, while the present disclosure provides a multi-piece implantable joint prosthesis comprising at least one joint prosthesis component having at least one coupler that is coupled to at least one adapter, and that adapter is also coupled to at least one precursor joint prosthesis, such as illustrated in FIGS. 2A through 6C, the present disclosure also provides that a joint prosthesis component may have more than one coupler, which may be referred to as a multi-coupler prosthesis joint component. In general, the joint prosthesis component may have X couplers where X is at least 1, and may be 2, or 3, or 4, or 5, or 6, or 7, or 8, or 9, or 10, or more than 10. Collectively, the X number of couplers will couple to as few as one adapter, or as many as X number of adapters. For example, in FIG. 7D, X is 2, so that each of the 2 couplers on the joint prosthesis component couples to a different adapter. As noted elsewhere herein, the present disclosure also provides medical implants wherein a precursor joint implant is coupled directly to a piece with electronic components, to provide an implantable medical device without an adapter.

Likewise, while a multi-piece implantable joint prosthesis of the present disclosure will comprise at least one precursor joint prosthesis having at least one coupler that is coupled to at least one adapter, and that adapter will also be coupled to at least one joint prothesis component, such as illustrated in FIGS. 2A through 6C, the present disclosure provides that a precursor joint prothesis may have more than one coupler, which may be referred to as a multi-coupler precursor joint prosthesis. In general, the precursor joint prosthesis may have Y couplers where Y is at least 1, and may be 2, or 3, or 4, or 5, or 6, or 7, or 8, or 9, or 10, or more than 10. Collectively, the Y number of couplers will couple to as few as one adapter, or as many as Y number of adapters. For example, in FIG. 7D, Y is 2, so that each of the 2 couplers on the precursor prosthesis couples to a different adapter.

Likewise, while a multi-piece implantable joint prosthesis of the present disclosure will comprise at least one adapter having at least two couplers, one of which couplers is coupled to a joint prosthesis component and the other coupler is coupled to a precursor joint component, such as illustrated in FIGS. 2A through 6C, the present disclosure provides that an adapter may have more than two couplers. For example, an adapter may have 3, or 4, or 5, or 6, or 7, or 8, or 9, or 10, or 11, or 12, or 13, or 14, or 15, or 16, or 17, or 18, or 19, or 20, or more than 20 couplers. When the multi-piece implantable joint prosthesis has a single adapter, then that adapter will have X+Y number of couplers. However, as mentioned, the multi-piece implantable joint prosthesis of the present disclosure may have more than one adapter, e.g., it may have 2, or 3, or 4, or 5, or 6, or 7, or 8, or 9, or 10, or more than 10 adapters. Each adapter will have at least two couplers. Collectively, the adapters present in a multi-piece implantable joint prosthesis of the present disclosure may have X+Y couplers.

Figure 8A:
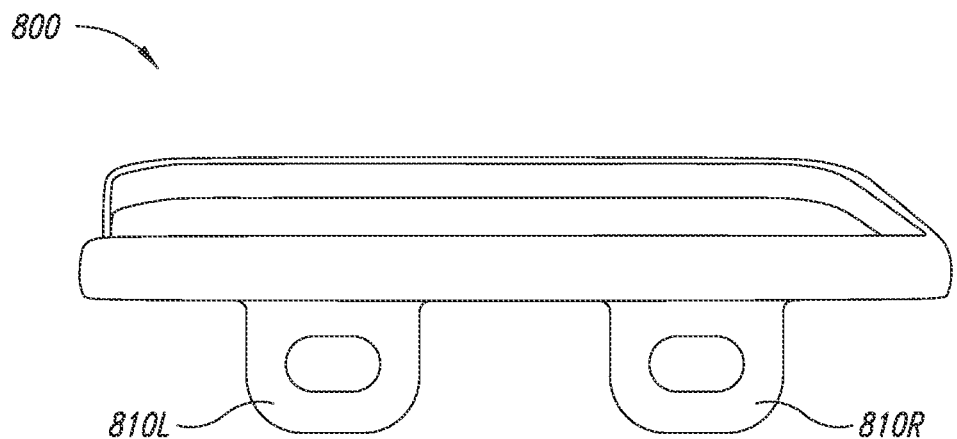
FIG. 8A is a perspective view of a partial tibial component of a knee prosthesis having a double keel.

FIG. 8A is a perspective view of a partial tibial component 800 of a knee prosthesis having a double keel 810L and 810R. The prosthesis 800 provides all the structural features needed for an effective implanted joint prosthesis.

Figure 8B:
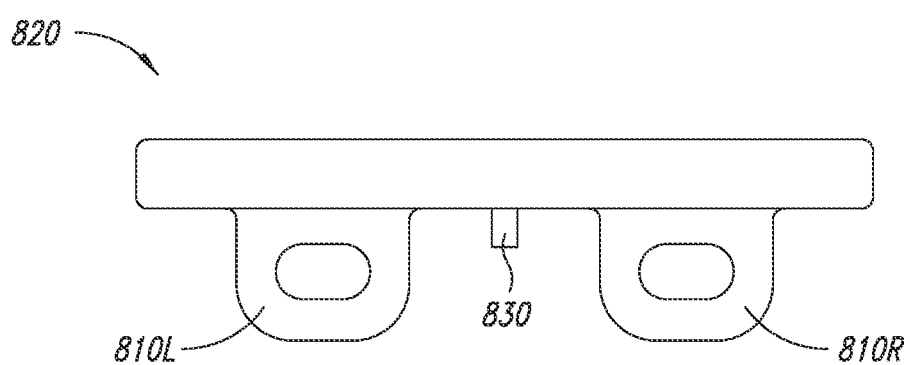
FIG. 8B is a schematic view of the partial tibial component of FIG. 8A to which has been added a coupling feature to provide a modified partial tibial component.
Figure 8C:
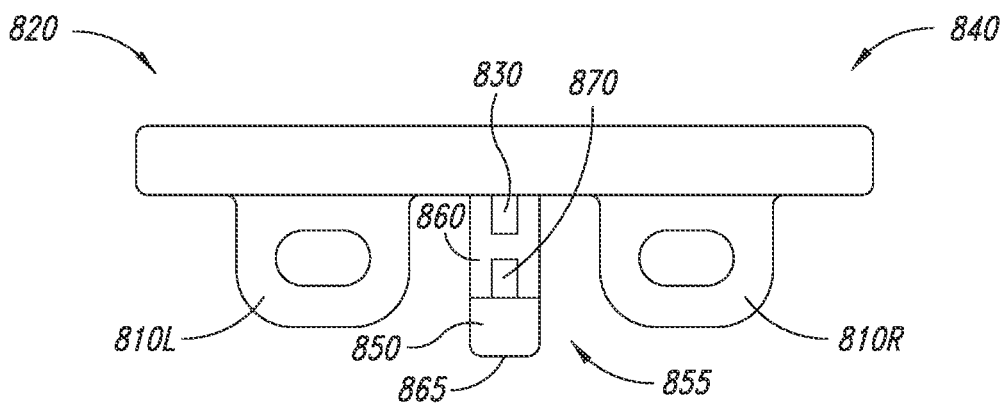
FIG. 8C is a schematic view of an expanded implantable joint prosthesis of the present disclosure, and more specifically an expanded implantable partial tibial component of a knee prosthesis formed from the modified partial tibial component of FIG. 8B coupled an adapted joint prosthesis component.

FIG. 8B is a schematic view of the partial tibial component 800 of FIG. 8A to which has been added a coupler 830 to thereby provide a precursor joint prosthesis 820. The precursor joint prosthesis 820 retains all essential features of the partial tibial component of a knee prosthesis 800, including the two keels 810L and 810R. The coupler 830 has a coupling configuration which may be used to couple the precursor joint prosthesis 820 to an adapted joint prosthesis component such as illustrated in FIG. 8C. The coupler 830 may be referred to as a fourth coupler, and the configuration of the coupler 830 may be referred to as a fourth coupling configuration, to thereby help distinguish coupler 830 from other couplers and coupling configuration present in a multi-piece implantable joint prosthesis of the present disclosure of which the precursor joint prosthesis 820 is a piece.

FIG. 8C is a schematic view of multi-piece implantable joint prosthesis 840 of the present disclosure, and more specifically multi-piece implantable partial tibial component of a knee prosthesis. The prosthesis 840 is formed from the precursor joint prosthesis 820 of FIG. 8B coupled an adapted joint prosthesis component 855. The adapted joint prosthesis component 855 comprises a joint prosthesis component 850 coupled to an adapter 860. The joint prosthesis component 850 comprising a housing 865, and within the housing is a body of the joint prosthesis component 850, where the body includes one or more electronic features such as a sensor, a power supply, a memory and a communication interface (not shown). The joint prosthesis component 850 also includes a coupler 870, illustrated in FIG. 8C as a post, which may be referred to as a first coupler, where the first coupler has a first coupling configuration. The first coupler 870 having a first coupling configuration can couple to the second coupler of the adapter 860 having a second coupling configuration, to provide the adapted joint prosthesis component 855. The adapted joint prosthesis 855 is coupled to the fourth coupler 830 of the precursor joint prosthesis 820 by way of the adapter 860, where a third coupler having a third coupling configuration of the adapter 860 is coupled to the fourth coupler 830 to thereby provide the multi-piece implantable joint prosthesis 840.

Figure 8D:
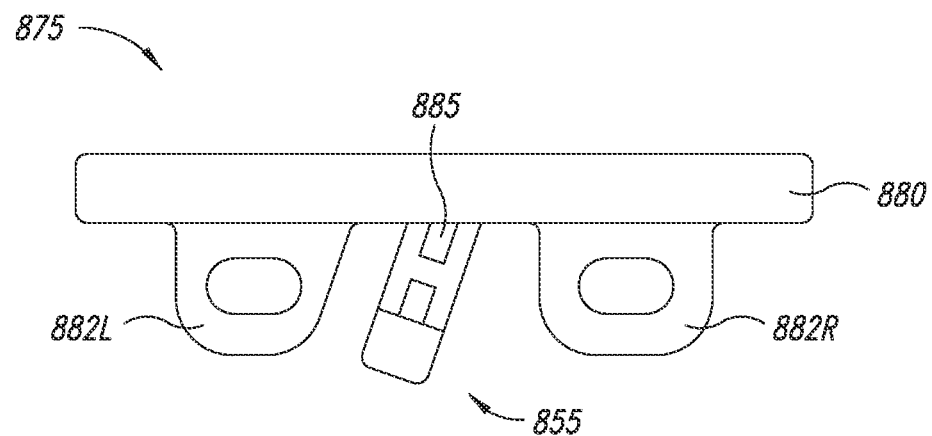
FIG. 8D is a schematic view of an expanded implantable joint prosthesis of the present disclosure, and more specifically an expanded implantable partial tibial component of a knee prosthesis formed from a modified partial tibial component having an asymmetrical double keel coupled to an adapted prosthesis component.

FIG. 8D is a schematic view of a multi-piece implantable joint prosthesis of the present disclosure, and more specifically a multi-piece implantable partial tibial component 875 of a knee prosthesis. The prosthesis component 875 is formed from a precursor joint prosthesis 880, and more specifically a precursor partial tibial component having an asymmetrical double keel with keels 882L and 882R and a coupler 885, illustrated as a post. The coupler 885 of the component 880 is located between the keels 882L and 882R but directed towards the keel 882L. To provide sufficient room for the placement of the coupler 885, the keel 882L has a reduced size compared to the keel 881R. Thus, the precursor joint prosthesis 880 has a double asymmetric keel. The coupler 885 may be referred to herein for convenience as the fourth coupler, to thereby distinguish the coupler 885 from other couplers present in the multi-piece implantable joint prosthesis 875. The precursor joint prosthesis 880 is coupled to an adapted joint prosthesis component 855 as previously described in relation to FIG. 8C to provide the multi-piece implantable joint prosthesis 875.

Thus, in one aspect, the present disclosure provides a precursor joint prosthesis, and more specifically a precursor partial tibial component having two keels and a coupler located therebetween, where the coupler is directed primarily towards one of the two keels, and the two keels are asymmetric, i.e., are not physically identical to one another. Each of the couplers present in the multi-piece implantable joint prosthesis, including pieces thereof, maybe optionally be selected from a Morris taper, a threaded rod, a polygonal rod, a cylindrical rod, a Bayonet Neill-Concelman (BNC), and a complement thereof.

In a related aspect, the present disclosure provides a multi-piece implantable joint prosthesis, e.g., an implantable partial tibial component of a knee prosthesis, comprising a precursor joint prosthesis coupled to an adapted joint prosthesis component, where the precursor joint prosthesis has two keels and a coupler (a fourth coupler) located therebetween, where the coupler is directed primarily towards one of the two keels, and the two keels are asymmetric, and where the coupler (the fourth coupler) is coupled to the adapted joint prosthesis component. The adapted joint prosthesis component comprises: a joint prosthesis component and an adapter, where the joint prosthesis component is coupled to the adapter. The joint prosthesis component comprises a housing with a body of the joint prosthesis component located within the body. The body of the joint prosthesis component comprises one or more electronic components selected from, for example, a sensor, a power supply, a memory and a communication interface. The joint prosthesis component also comprises a coupler (a first coupler) having a coupling configuration (a first coupling configuration) to couple the joint prosthesis component to the adapter. The adapter comprises a second coupler having a second coupling configuration and a third coupler having a third coupling configuration. A first coupling mechanism couples the first coupling configuration of the first coupler of the joint prosthesis component to the second coupling configuration of the second coupler of the adapter to provide the adapted joint prosthesis component.

Each of the couplers present in the multi-piece implantable joint prosthesis, including pieces thereof, maybe optionally be selected from a Morris taper, a threaded rod, a polygonal rod, a cylindrical rod, a Bayonet Neill-Concelman (BNC), and a complement thereof. Each of the coupling mechanisms utilized in forming the multi-piece implantable joint prosthesis may independently be selected from: welding, a threaded coupling, a mechanical coupling selected from interference fit (a.k.a. press fit, friction fit) and bolting, and adhesive bonding.

Figure 8E:
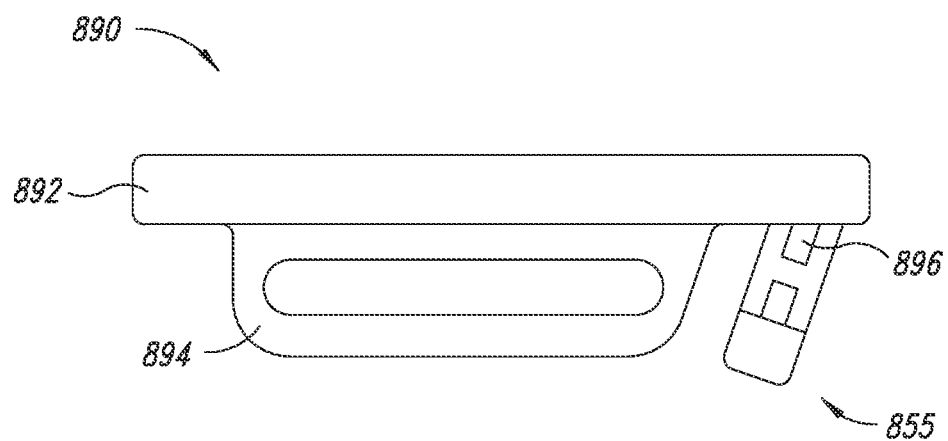
FIG. 8E is a schematic view of an expanded implantable joint prosthesis of the present disclosure, and more specifically an expanded implantable partial tibial component of a knee prosthesis formed from a modified partial tibial component having a offset single keel coupled to an adapted joint prosthesis component.

FIG. 8E is a schematic view of a multi-piece implantable joint prosthesis of the present disclosure, and more specifically a multi-piece implantable partial tibial component 890 of a knee prosthesis formed from a precursor joint prosthesis and more specifically a precursor partial tibial prosthesis 892. The prosthesis 892 has an asymmetrical single keel 894 and a coupler 896. The coupler 896 may be referred to for convenience as the fourth coupler, to distinguish this coupler 896 from other couplers present in the multi-piece implantable joint prosthesis 890. The coupler 896 is directed towards the single keel 894 and for this reason the single keel 894 has an asymmetric configuration so that the coupler 896 does not contact the single keel 894. The precursor joint prosthesis 892 is coupled to an adapted joint prosthesis component 855 which has previously been described in relation to FIG. 8C.

Thus, in one aspect, the present disclosure provides a precursor joint prosthesis, and more specifically a precursor partial tibial prosthesis having a single asymmetric keel and a coupler located next to but not touching the asymmetric keel, where the coupler is directed towards the asymmetric keel. The coupler may be described by its coupling configuration which may be selected from a Morris taper, a threaded rod, a polygonal rod, a cylindrical rod, a Bayonet Neill-Concelman (BNC), and a complement thereof.

In a related aspect, the present disclosure provides a multi-piece implantable joint prosthesis, and more specifically a multi-piece implantable partial tibial component of a knee prosthesis comprising a precursor joint prosthesis coupled to an adapted joint prosthesis component. The precursor joint prosthesis is a precursor partial tibial component that has a single asymmetric keel and a coupler located next to but not touching the asymmetric keel, where the coupler is directed towards the asymmetric keel. The coupler of the precursor joint prosthesis is coupled to the adapted joint prosthesis component. The adapted joint prosthesis component comprises: a joint prosthesis component and an adapter, where the joint prosthesis component is coupled to the adapter. The joint prosthesis component comprises a housing with a body of the joint prosthesis component located within the body. The body of the joint prosthesis component comprises one or more electronic components selected from, for example, a sensor, a power supply, a memory and a communication interface. The joint prosthesis component also comprises a coupler (a first coupler) having a coupling configuration (a first coupling configuration) to couple the joint prosthesis component to the adapter. The adapter comprises a second coupler having a second coupling configuration and a third coupler having a third coupling configuration. A first coupling mechanism couples the first coupling configuration of the first coupler of the joint prosthesis component to the second coupling configuration of the second coupler of the adapter to provide the adapted joint prosthesis component.

In one aspect (not shown) a multi-piece implantable joint prosthesis comprising precursor joint prosthesis 820 may further comprise a piece having electronic components 850 and 860, where that piece couples directly to the precursor joint prosthesis 820, without an intervening adaptor. Likewise, in one aspect (not shown) a multi-piece implantable joint prosthesis comprising precursor joint prosthesis 880 may further comprise a piece having electronic components that couples directly to the precursor joint prosthesis 880 via the connector 885, without an intervening adaptor. Likewise, in one aspect (not shown) a multi-piece implantable joint prosthesis comprising precursor joint prosthesis 892 may further comprise a piece having electronic components that couples directly to the precursor joint prosthesis 892 via the connector 896, without an intervening adaptor.

In one embodiment of the expanded implantable partial tibial component of a knee prosthesis of the present disclosure, the first coupling configuration is different from the third coupling configuration.

In one embodiment of the expanded implantable partial tibial component of a knee prosthesis of the present disclosure, the first coupling configuration and the third coupling configuration are each independently selected from a Morris taper, a threaded rod, a polygonal rod, a cylindrical rod, a Bayonet Neill-Concelman (BNC), and a complement thereof.

In one embodiment of the expanded implantable partial tibial component of a knee prosthesis of the present disclosure, the first coupling mechanism and/or the second coupling mechanism comprises welding.

In one embodiment of the expanded implantable partial tibial component of a knee prosthesis of the present disclosure, the first coupling mechanism and/or the second coupling mechanism comprises a threaded coupling.

In one embodiment of the expanded implantable partial tibial component of a knee prosthesis of the present disclosure, the first coupling mechanism and/or the second coupling mechanism is a mechanical coupling selected from interference fit (a.k.a. press fit, friction fit) and bolting.

In one embodiment of the expanded implantable partial tibial component of a knee prosthesis of the present disclosure, the first coupling mechanism and/or the second coupling mechanism is adhesive bonding.

The implantable medical device of the present disclosure, e.g., the multi-piece implantable joint prosthesis of the present disclosure, may be part of an environment which communicates with implanted medical device. An exemplary environment is an operating room wherein the implantable medical device is being implanted into a patient by a health care profession.

Another exemplary environment is the patient's home, in the case where the implantable medical device has already been implanted in the patient. Yet another exemplary environment is a doctor's office, where the patient having the implanted medical device is in the office for, e.g., an evaluation. The following provides a detailed description of an exemplary environment in a patient's home. However, the described features and connectivity are analogously present in other environments within which the patient with the implanted medical device is present, e.g., the operating room and the doctor's office, as also described herein albeit in lesser detail.

Figure 9:
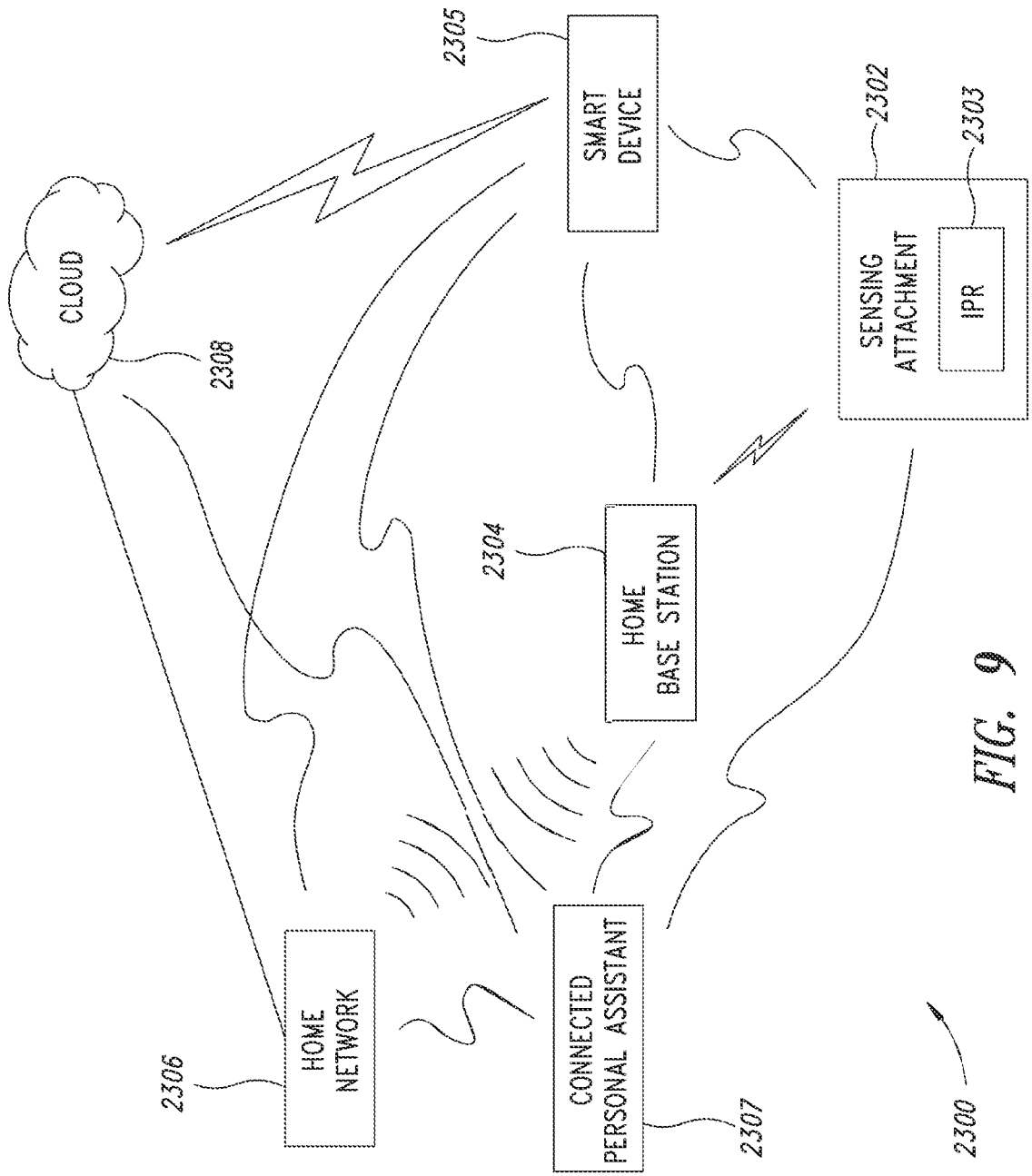
FIG. 9 is a context diagram of an implanted medical device environment in a patient's home.

FIG. 9 illustrates a context diagram of a smart medical device environment 2300 including features present in the patient's home. In FIG. 9, the implanted medical device of the present disclosure, which may be, e.g., an implanted multi-piece implantable joint prosthesis, is referred to as a smart medical device (2303). The IRP (Implantable Reporting Processor) in FIG. 9 refers to the electronic component of the implantable medical device or piece thereof as disclosed herein.

In the environment, a smart medical device 2302 comprising an implantable reporting processor (IPR) 2303 has been implanted into a patient (not shown). Taken together, the sensing capability and the associated electronics assembly of the smart medical device of the present disclosure may be referred to as an implantable reporting processor (IPR). The IPR is a component of the smart medical device of the present disclosure, where the smart medical device comprises the IPR. An antenna may or may not be a component of the IPR. Likewise, a power supply may not be a component of the IPR. The implantable reporting processor 2303 is arranged and configured to collect data including for example, medical and health data related to a patient which the device is associated, and operational data of the smart medical device 2302 itself. The smart medical device 2302 communicates with one or more home base stations 2304 or one or more external smart devices 2305 during different stages of monitoring the patient.

The smart medical device 2302 includes one or more sensors that collect information and data, including medical and health data related to a patient which the device is associated, and operational data of the medical device 2302 itself. The smart medical device 2302 collects data at various different times and at various different rates during a monitoring process of the patient, and may optionally store that data in a memory until it is transmitted outside the body of the patient. In some embodiments, the smart medical device 2302 may operate in a plurality of different phases over the course of monitoring the patient so that more data is collected soon after the smart medical device 2302 is implanted into the patient, but less data is collected as the patient heals and thereafter.

The amount and type of data collected by the smart medical device 2302 may be different from patient to patient, and the amount and type of data collected may change for a single patient. For example, a medical practitioner studying data collected by the smart medical device 2302 of a particular patient may adjust or otherwise control how the smart medical device 2302 collects future data.

The amount and type of data collected by a smart medical device 2302 may be different for different body parts, for different types of patient conditions, for different patient demographics, or for other differences. Alternatively, or in addition, the amount and type of data collected may change overtime based on other factors, such as how the patient is healing or feeling, how long the monitoring process is projected to last, how much power remains in the smart medical device 2302 and should be conserved, the type of movement being monitored, the body part being monitored, and the like. In some cases, the collected data is supplemented with personally descriptive information provided by the patient such as subjective pain data, quality of life metric data, co-morbidities, perceptions or expectations that the patient associates with the smart medical device 2302, or the like.

Once the smart medical device 2302 is implanted into the patient and the patient returns home, the smart medical device may begin communications outside of the patient's body, within the home environment. The communication may be with, e.g., the home base station 2304, the external smart device 2305 (e.g., the patient's smart phone), the connected personal assistant 2307, or two or more of the home base station, and the external smart device, and the connected personal assistant can communicate with the smart medical device 2302. The smart medical device 2302 can collect data at determined rates and times, variable rates and times, or otherwise controllable rates and times. Data collection can start when the smart medical device 2302 is initialized in the operating room, when directed by a medical practitioner, or at some later point in time.

At least some data collected by the smart medical device 2302 may be transmitted to the home base station 2304 directly, to the external smart device 2305 directly, to the connected personal assistant 2307 directly, to the base station via one or both of the smart device and the connected personal assistant, to the smart device via one or both of the base station and the connected personal assistant, or to the connected personal assistant via one or both of the smart device and the base station. Here, "one or both" means via an item alone, and via both items serially or in parallel. For example, data collected by the implanted smart medical device 2302 may be transmitted to the home base station 2304 via the external smart device 2305 alone, via the connected personal assistant 2307 alone, serially via the external smart device and the connected personal assistant, serially via the connected personal assistant and the external smart device, and directly, and possibly contemporaneously, via both the external smart device and the connected personal assistant.

Similarly, data collected by the implanted smart medical device 2302 may be transmitted to the external smart device 2305 via the home base station 2304 alone, via the connected personal assistant 2307 alone, serially via the home base station and the connected personal assistant, serially via the connected personal assistant and the home base station, and directly, and possibly contemporaneously, via both the home base station and the connected personal assistant. Further in example, data collected by the implanted smart medical device 2302 may be transmitted to the connected personal assistant 2307 via the external smart device 2305 alone, via the home base station 2304 alone, serially via the external smart device and the home base station, serially via the home base station and the external smart device, and directly, and possibly contemporaneously, via both the external smart device and the home base station.

In various embodiments, one or more of the home base station 2304, the external smart device 2305, and the connected personal assistant 2307 pings the implanted smart medical device 2302 at periodic, predetermined, or other times to determine if the implanted smart medical device 2302 is within communication range of one or more of the home base station, the external smart device, and the connected personal assistant. Based on a response from the implanted smart medical device 2302, one or more of the home base station 2304, the external smart device 2305, and the connected personal assistant 2307 determines that the implanted smart medical device 2302 is within communication range, and the implanted smart medical device 2302 can be requested, commanded, or otherwise directed to transmit the data it has collected to one or more of the home base station 2304, the external smart device 2305, and the connected personal assistant 2307.

Each of one or more of the home base station 2304, the external smart device 2305, and the connected personal assistant 2307 may, in some cases, be arranged with a respective optional user interface. The user interface may be formed as a multimedia interface that unidirectionally or bi-directionally passes one or more types of multimedia information (e.g., video, audio, tactile, etc.). Via the respective user interface of one or more of the home base station 2304, the external smart device 2305, and the connected personal assistant 2307, the patient (not shown in FIG. 9) or an associate (not shown in FIG. 9) of the patient may enter other data to supplement the data collected by the implanted smart medical device 2302. A user, for example, may enter personally descriptive information (e.g., age change, weight change), changes in medical condition, co-morbidities, pain levels, quality of life, an indication of how the implanted smart medical device 2302 "feels," or other subjective metric data, personal messages for a medical practitioner, and the like. In these embodiments, the personally descriptive information may be entered with a keyboard, mouse, touch-screen, microphone, wired or wireless computing interface, or some other input means. In cases where the personally descriptive information is collected, the personally descriptive information may include, or otherwise be associated with, one or more identifiers that associate the information with unique identifier of the implanted smart medical device 2302, the patient, an associated medical practitioner, an associated medical facility, or the like.

In some of these cases, a respective optional user interface of each of one or more of the home base station 2304, the external smart device 2305, and the connected personal assistant 2307 may also be arranged to deliver information associated with the implanted smart medical device 2302 to the user from, for example, a medical practitioner. In these cases, the information delivered to the user may be delivered via a video screen, an audio output device, a tactile transducer, a wired or wireless computing interface, or some other like means.

In embodiments where one or more of the home base station 2304, the external smart device 2305, and the connected personal assistant 2307 are arranged with a user interface, which may be formed with an internal user interface arranged for communicative coupling to a patient portal device. The patent portal device may be smartphone, a tablet, a body-worn device, a weight or other health measurement device (e.g., thermometer, bathroom scale, etc.), or some other computing device capable of wired or wireless communication. In these cases, the user is able to enter the personally descriptive information, and the user also may be able to receive information associated with the implanted smart medical device 2302.

The home base station 2304 utilizes a home network 2306 of the patient to transmit the collected data to cloud 2308. The home network 2306, which may be a local area network, provides access from the home of the patient to a wide area network, such as the internet. In some embodiments, the home base station 2304 may utilize a Wi-Fi connection to connect to the home network 2306 and access the internet. In other embodiments, the home base station 2304 may be connected to a home computer (not shown in FIG. 9) of the patient, such as via a USB connection, which itself is connected to the home network 2306.

The external smart device 2305 can communicate with the implanted smart medical device 2302 directly via, for example, Blue Tooth® compatible signals, and can utilize the home network 2306 of the patient to transmit the collected data to cloud 2308, or can communicate directly with the cloud, for example, via a cellular network. Alternatively, the external smart device 2305 is configured to communicate directly with one or both of the home base station 2304 and the connected personal assistant 2307 via, for example, Blue Tooth® compatible signals, and is not configured to communicate directly with the implanted smart medical device 2302.

Furthermore, the connected personal assistant 2307 can communicate with the implanted smart medical device 2302 directly via, for example, Blue Tooth® compatible signals, and can utilize the home network 2306 of the patient to transmit the collected data to cloud 2308, or can communicate directly with the cloud, for example, via a modem/internet connection or a cellular network. Alternatively, the connected personal assistant 2307 is configured to communicate directly with one or both of the home base station 2304 and the external smart device 2305 via, for example, Blue Tooth® compatible signals, and is not configured to communicate directly with the implanted smart medical device 2302.

Along with transmitting collected data to the cloud 2308, one or more of the home base station 2304, the external smart device 2305, and the connected personal assistant 2307 may also obtain data, commands, or other information from the cloud 2308 directly or via the home network 2306. One or more of the home base station 2304, the external smart device 2305, and the connected personal assistant 2307 may provide some or all of the received data, commands, or other information to the implanted smart medical device 2302. Examples of such information include, but are not limited to, updated configuration information, diagnostic requests to determine if the implanted smart medical device 2302 is functioning properly, data collection requests, and other information.

The cloud 2308 may include one or more server computers or databases to aggregate data collected from the implanted smart medical device 2302, and in some cases personally descriptive information collected from a patient (not shown in FIG. 9), with data collected from other assemblies (not illustrated), and in some cases personally descriptive information collected from other patients. In this way, the cloud 2308 can create a variety of different metrics regarding collected data from each of a plurality of assemblies that are implanted into separate patients. This information can be helpful in determining if the assemblies are functioning properly. The collected information may also be helpful for other purposes, such as determining which specific devices may not be functioning properly, determining if a procedure or condition associated with the smart medical device is helping the patient (e.g., if the knee replacement is operating properly and reducing the patient's pain), and determining other medical information.

Still referring to FIG. 9, alternate embodiments are contemplated. For example, one or two of the home base station 2304, the external smart device 2305, and the connected personal assistant 2307 may be omitted from the smart medical device environment 2300. Furthermore, each of the home base station 2304, the external smart device 2305, and the connected personal assistant 2307 may be configured to communicate with one or both of the implanted smart medical device 2302 and the cloud 2308 via another one or two of the base station, the smart device, and the connected personal assistant. Moreover, the external smart device 2305 can be temporarily contracted as an interface to the implanted smart medical device 2302, and can be any suitable device other than a smart phone, such as a smart watch, a smart patch, and any IoT device, such as a coffee pot, capable of acting as an interface to the implanted smart medical device 2302.

In addition, one or more of the home base station 2304, external smart device 2305, and connected personal assistant 2307 can act as a communication hub for multiple prostheses implanted in one or more patients. Furthermore, one or more of the home base station 2304, external smart device 2305, and connected personal assistant 2307 can automatically order or reorder prescriptions or medical supplies (e.g., a knee brace) in response to patient input or implantable-prosthesis input (e.g., pain level, instability level) if a medical professional and insurance company have preauthorized such an order or reorder; alternatively, one or more of the base station, smart device, and connected personal assistant can be configured to request, from a medical professional or an insurance company, authorization to place the order or reorder. Moreover, one or more of the home base station 2304, external smart device 2305, and connected personal assistant 2307 can be configured with a personal assistant such as Alexa® or Siri®.

Although the smart medical device environment has been described in the context of a patient's home by reference to FIG. 9, the same principles apply when the environment is an operating room or a doctor's office. For example, in association with a medical procedure, a implanted smart medical device 2302 may be implanted in the patient's body within an operating room environment. Coetaneous with the medical procedure, the implanted smart medical device 2302 communicates with an operating room base station (analogous to the home base station). Subsequently, after sufficient recovery from the medical procedure, the patient returns home wherein the implanted smart medical device 2302 is arranged to communicate with a home base station 2304. Thereafter, at other times, the implanted smart medical device 2302 is arranged to communicate with a doctor office base station when the patient visits the doctor for a follow-up consultation. In any case, the implanted smart medical device 2302 communicates with each base station via a short range network protocol, such as the medical implant communication service (MICS), the medical device radio communications service (MedRadio), or some other wireless communication protocol suitable for use with the smart medical device 2302.

For example, implantation of the implanted smart medical device 2302 into the patient may occur in an operating room. As used herein, operating room includes any office, room, building, or facility where the smart medical device 2302 is implanted into the patient. For example, the operating room may be a typical operating room in a hospital, an operating room in a surgical clinic or a doctor's office, or any other operating theater where the smart medical device 2302 is implanted into the patient.

The operating room base station (analogous to the home base station of FIG. 9) is utilized to configure and initialize the implanted smart medical device 2302 in association with the smart medical device 2302 being implanted into the patient. A communicative relationship is formed between the smart medical device 2302 and the operating room base station, for example, based on a polling signal transmitted by the operating room base station and a response signal transmitted by the smart medical device 2302.

Upon forming a communicative relationship, which will often occur prior to implantation of the smart medical device 2302, the operating room base station transmits initial configuration information to the smart medical device 2302. This initial configuration information may include, but is not limited to, a time stamp, a day stamp, an identification of the type and placement of the smart medical device 2302, information on other implants associated with the smart medical device, surgeon information, patient identification, operating room information, and the like.

In some embodiments, the initial configuration information is passed unidirectionally; in other embodiments, initial configuration is passed bidirectionally. The initial configuration information may define at least one parameter associated with the collection of data by the smart medical device 2302. For example, the configuration information may identify settings for one or more sensors on the smart medical device 2302 for each of one or more modes of operation. The configuration information may also include other control information, such as an initial mode of operation of the smart medical device 2302, a particular event that triggers a change in the mode of operation, radio settings, data collection information (e.g., how often the smart medical device 2302 wakes up to collected data, how long it collects data, how much data to collect), home base station 2304, smart device 2305, and connected personal assistant 2307 identification information, and other control information associated with the implantation or operation of the smart medical device 2302. Examples of the connected personal assistant 2307, which also can be called a smart speaker, include Amazon Echo®, Amazon Dot®, Google Home®, Philips® patient monitor, Comcast's health-tracking speaker, and Apple HomePod®.

In some embodiments, the configuration information may be pre-stored on the operating room base station or an associated computing device. In other embodiments, a surgeon, surgical technician, or some other medical practitioner may input the control information and other parameters to the operating room base station for transmission to the smart medical device 2302. In at least one such embodiment, the operating room base station may communicate with an operating room configuration computing device. The operating room configuration computing device includes an application with a graphical user interface that enables the medical practitioner to input configuration information for the smart medical device 2302. In various embodiments, the application executing on the operating room configuration computing device may have some of the configuration information predefined, which may or may not be adjustable by the medical practitioner.

The operating room configuration computing device communicates the configuration information to the operating room base station via a wired or wireless network connection (e.g., via a USB connection, Bluetooth connection, Bluetooth Low Energy (BTLE) connection, or Wi-Fi connection), which in turn communicates it to the smart medical device 2302.

The operating room configuration computing device may also display information regarding the smart medical device 2302 or the operating room base station to the surgeon, surgical technician, or other medical practitioner. For example, the operating room configuration computing device may display error information if the smart medical device 2302 is unable to store or access the configuration information, if the smart medical device 2302 is unresponsive, if the smart medical device 2302 identifies an issue with one of the sensors or radio during an initial self-test, if the operating room base station is unresponsive or malfunctions, or for other reasons.

Although the operating room base station and the operating room configuration computing device are described as separate devices, embodiments are not so limited; rather, the functionality of the operating room configuration computing device and the operating room base station may be included in a single computing device or in separate devices as illustrated. In this way, the medical practitioner may be enabled in one embodiment to input the configuration information directly into the operating room base station.

After the smart medical device has been implanted in the patient, the patient may periodically visit a doctor's office for follow-up evaluation. In one aspect, the present disclosure provides a doctor's office environment (analogous to the home environment described herein) wherein the implanted smart medical device communicates with the office environment. During these visits, the data that has been stored in memory may be accessed, and/or specific data may be requested and obtained as part of a monitoring process.

For example, at various times throughout the monitoring process, the patient may be requested to visit a medical practitioner for follow up appointments. This medical practitioner may be the surgeon who implanted the smart medical device 2302 in the patient or a different medical practitioner that supervises the monitoring process, physical therapy, and recovery of the patient. For a variety of different reasons, the medical practitioner may want to collect real-time data from the smart medical device 2302 in a controlled environment. In some cases, the request to visit the medical practitioner may be delivered through a respective optional bidirectional user interface of each of one or more of the home base station 2304, the external smart device 2305, and the connected personal assistant 2307.

A medical practitioner utilizes the doctor office base station (analogous to the home base station shown in FIG. 9), which communicates with the smart medical device 2302, to pass additional data between the doctor office base station and the smart medical device 2302. Alternatively, or in addition, the medical practitioner utilizes the doctor office base station (not shown in FIG. 9) to pass commands to the smart medical device 2302. In some embodiments, the doctor office base station instructs the smart medical device 2302 to enter a high-resolution mode to temporarily increase the rate or type of data that is collected for a short time. The high-resolution mode directs the smart medical device 2302 to collect different (e.g., large) amounts of data during an activity where the medical practitioner is also monitoring the patient.

In some embodiments, the doctor office base station enables the medical practitioner to input event or pain markers, which can be synchronized with the high-resolution data collected by the smart medical device 2302. For example, the medical practitioner can have the patient walk on a treadmill while the smart medical device 2302 is in the high-resolution mode. As the patient walks, the patient may complain about pain. The medical practitioner can click a pain marker button on the doctor office base station to indicate the patient's discomfort. The doctor office base station records the marker and the time at which the marker was input. When the timing of this marker is synchronized with the timing of the collected high-resolution data, the medical practitioner can analyze the data to try and determine the cause of the pain.

In other embodiments, the doctor office base station may provide updated configuration information to the smart medical device 2302. The smart medical device 2302 can store this updated configuration information, which can be used to adjust the parameters associated with the collection of the data. For example, if the patient is doing well, the medical practitioner can direct a reduction in the frequency at which the smart medical device 2302 collects data. On the contrary, if the patient is experiencing an unexpected amount of pain, the medical practitioner may direct the smart medical device 2302 to collect additional data for a determined period of time (e.g., a few days). The medical practitioner may use the additional data to diagnose and treat a particular problem. In some cases, the additional data may include personally descriptive information provided by the patient after the patient has left presence of the medical practitioner and is no longer in range of the doctor office base station. In these cases, the personally descriptive information may be collected and delivered from via one or more of the home base station 2304, the external smart device 2305, and the connected personal assistant 2307. Firmware within the smart medical device and/or the base station will provide safeguards limiting the duration of such enhanced monitoring to ensure the smart medical device 2302 retains sufficient power to last for the implant's lifecycle.

In various embodiments, the doctor office base station may communicate with a doctor office configuration computing device (analogous to the operating room computing device). The doctor office configuration computing device includes an application with a graphical user interface that enables the medical practitioner to input commands and data. Some or all of the commands, data, and other information may be later transmitted to the smart medical device 2302 via the doctor office base station. For example, in some embodiments, the medical practitioner can use the graphical user interface to instruct the smart medical device 2302 to enter its high-resolution mode. In other embodiments, the medical practitioner can use graphical user interface to input or modify the configuration information for the smart medical device 2302. The doctor office configuration computing device transmits the information (e.g., commands, data, or other information) to the doctor office base station via a wired or wireless network connection (e.g., via a USB connection, Bluetooth connection, or Wi-Fi connection), which in turn transmits some or all of the information to the smart medical device 2302.

The doctor office configuration computing device may also display, to the medical practitioner, other information regarding the smart medical device 2302, regarding the patient (e.g., personally descriptive information), or the doctor office base station. For example, the doctor office configuration computing device may display the high-resolution data that is collected by the smart medical device 2302 and transmitted to the doctor office base station. The doctor office configuration computing device may also display error information if the smart medical device 2302 is unable to store or access the configuration information, if the smart medical device 2302 is unresponsive, if the smart medical device 2302 identifies an issue with one of the sensors or radio, if the doctor office base station is unresponsive or malfunctions, or for other reasons.

In some embodiments, doctor office configuration computing device may have access to the cloud 2308. In at least one embodiment, the medical practitioner can utilize the doctor office configuration computing device to access data stored in the cloud 2308, which was previously collected by the smart medical device 2302 and transmitted to the cloud 2308 via one or both of the home base station 2304 and external smart device 2305. Similarly, the doctor office configuration computing device can transmit the high-resolution data obtain from the smart medical device 2302 via the doctor office base station to the cloud 2308. In some embodiments, the doctor office base station may have internet access and may be enabled to transmit the high-resolution data directly to the cloud 2308 without the use of the doctor office configuration computing device.

In various embodiments, the medical practitioner may update the configuration information of the smart medical device 2302 when the patient is not in the medical practitioner's office. In these cases, the medical practitioner can utilize the doctor office configuration computing device (not shown in FIG. 9) to transmit updated configuration information to the smart medical device 2302 via the cloud 2308. One or more of the home base station 2304, the external smart device 2305, and the connected personal assistant 2307 can obtain updated configuration information from the cloud 2308 and pass updated configuration information to the cloud. This can allow the medical practitioner to remotely adjust the operation of the smart medical device 2302 without needing the patient to come to the medical practitioner's office. This may also permit the medical practitioner to send messages to the patient in response, for example, to personally descriptive information that was provided by the patient and passed through one or more of the home base station 2304, the external smart device 2305, and the connected personal assistant 2307 to the doctor office base station (not shown in FIG. 9). For example, if a patient speaks "I feel pain" into the connected personal assistant 2307, then the medical practitioner may issue a prescription for a pain reliever and cause the connected personal assistant to notify the patient by "speaking" "the doctor has called in a prescription for Vicodin® to your preferred pharmacy; the prescription will be ready for pick up at 4 pm."

Although the doctor office base station (not shown in FIG. 9) and the doctor office configuration computing device (not shown in FIG. 9) are described as separate devices, embodiments are not so limited; rather, the functionality of the doctor office configuration computing device and the doctor office base station may be included in a single computing device or in separate devices (as illustrated). In this way, the medical practitioner may be enabled in one embodiment to input the configuration information or markers directly into the doctor office base station and view the high-resolution data (and synchronized marker information) from a display on the doctor office base station.

The following are exemplary electronic components that may be included in a piece of a multi-piece implantable medical device of the present disclosure.

In some embodiments, electronic component includes a power supply. The power supply of the electronic component may optionally be any suitable battery, such as a Lithium Carbon Monofluoride (LiCFx) battery, or other storage cell configured to store energy for powering components of the electronics assembly for an expected lifetime (e.g., 5-25+ years) of the implanted medical device. In some embodiment, the power supply may be a supercapacitor. Supercapacitors are attractive due to their fast charge/discharge characteristics, e.g., 2.8 mAh battery is rated at 0.2 C charge/discharge→5 hours charge time. They also have increased current delivery capability compared to batteries. The supercapacitor may be an electrochemical double layer capacitor (EDLC) supercapacitor or a wire shaped supercapacitor. Commercially available EDLCs are only half the volumetric energy density of "advanced" wired shaped supercapacitors. Accordingly, wire shaped supercapacitors may be preferred. In some embodiments, the power supply may be a hybrid solution. In this configuration, the electronic component includes a first power supply, e.g., a primary battery, for measurements, and a second power supply, e.g., a supercapacitor, for temporarily buffering energy while exchanging data. The power supply may be a rechargeable power device, such as a lithium-ion battery or a supercapacitor. In this case, the power supply and/or the electronics assembly includes additional components for charging the power source by an external recharge unit. These additional components may include a power coil configured to generate a voltage and current in response to a magnetic field generated by an external recharge unit. Possible modes of energy transfer include a far-field RF, near-field RF and ultrasonic. In one embodiment the power supply is or includes an energy harvester. The energy harvester is configured to convert an environmental stimulus into an energy for charging a rechargeable power device. For example, the harvester may convert, into a battery-charging electrical current or voltage or a supercapacitor-charging, one or more of body heat from the subject in which the device is implanted, kinetic energy generated by the subject's movement, changes in pressure (e.g., barometric pressure or pressure within the subject, such as the subject's blood pressure), energy generated by an electrochemical reaction within the subject's body, energy generated by radio-frequency (RF) fields, light, electro-mechanical conversion (such as piezoelectric), or electro-magnetic conversion.

In some embodiments, electronic component includes a circuit breaker, e.g., a fuse. The fuse can be any suitable fuse (e.g., permanent) or circuit breaker (e.g., resettable) configured to prevent the power supply or a current flowing from the battery, from injuring the patient and damaging the battery and one or more components of the electronics assembly. For example, the fuse can be configured to prevent the power supply from generating enough heat to burn the patient, to damage the electronics assembly, to damage the battery, or to damage structural components of the intelligent implantable implant.

In some embodiments, electronic component includes a power switch. A first power switch may be configured to couple the power supply to, or to uncouple the power supply from, the one or more sensors in response to a control signal from a controller. For example, the controller may be configured to generate the control signal having an open state that causes the switch to open, and, therefore, to uncouple power from the one or more sensors, during a sleep mode or other low-power mode to save power, and, therefore, to extend the life of the power supply. Likewise, the controller also may be configured to generate the control signal having a closed state that causes the switch to close, and therefore, to couple power to the one or more sensors, upon "awakening" from a sleep mode or otherwise exiting another low-power mode. Such a low-power mode may be for only the one or more sensors or for the sensors and one or more other components of the electronics assembly.

A second power switch may be configured to couple the power supply to, or to uncouple the power supply from, the memory in response to a control signal from the controller. For example, the controller may be configured to generate the control signal having an open state that causes the switch to open, and, therefore, to uncouple power from the memory, during a sleep mode or other low-power mode to save power, and, therefore, to extend the life of the power supply. Likewise, the controller also may be configured to generate the control signal having a closed state that causes the switch to close, and therefore, to couple power to the memory, upon "awakening" from a sleep mode or otherwise exiting another low-power mode. Such a low-power mode may be for only the memory or for the memory and one or more other components of the electronics assembly.

In some embodiments, electronic component includes a clock and power management unit. The clock and power management unit can be configured to generate a clock signal for one or more of the other components of the electronics assembly, and can be configured to generate periodic commands or other signals (e.g., interrupt requests) in response to which the controller causes one or more components of the electronic component to enter or to exit a sleep, or other low-power, mode. The clock and power management unit also can be configured to regulate the voltage from the power supply, and to provide a regulated power-supply voltage to some or all of the other components of the electronics assembly.

In some embodiments, electronic component includes a memory. The memory may include volatile memory and non-volatile memory. For example, the volatile memory may be configured to store the operating system and one or more applications executed by the controller. The non-volatile memory may be configured to store configuration information for the electronic component and to store data written by the controller, and to provide data in response to a read command from the controller.

In some embodiments, the electronic component includes a communication interface, which facilitates communication between the medical device and another device. The other device may be, for example, an external device, e.g., a base station, that is located outside of or away from the patient who has received the medical device, or it may be an internal device that is located in the patient who has received the medical device. In either case, communication between an implanted medical device and another device, whether internal or external, is referred to as intra-body communication. One or modes of intra-body communication may be enabled by the communication interface. Possible modes of intra-body communication include: 1) RF telemetry communication, 2) tissue conductive communication, e.g., galvanic coupling communication, and 3) data-over-sound communication, e.g. ultrasound or acoustic communication.

The communication interface includes communication circuitry that is generally, but not necessarily, associated with the electronics assembly of the IRP electronic component. The communication circuitry may include any hardware, firmware, software or any combination thereof suitable for enabling one or more modes of intra-body communication. To this end, the communication circuitry may include, for example, voltage regulators, current generators, oscillators, or circuitry for generating a signal, resistors, capacitors, inductors, and other filtering circuitry for processing received signals, as well as circuitry for modulating and/or demodulating a signal according to a communication protocol.

Depending on the mode of intra-body communication, the communication circuitry may also include transistors or other switching circuitry for selectively coupling transmitted signals to or receiving signals from a desired transceiver, such as an antenna 2030 (which may be used for electro-magnetic communication, e.g., RF telemetry communication) or electrodes (which may be used for tissue conductive communication) or an acoustic transducer (which may be used for data-over-sound communication). Under the control of the controller, communication circuitry may receive downlink communication signals from, as well as send uplink communication signals to, an external device or another implanted device. In addition, communication circuitry may communicate with a networked computing device via an external device and a computer network, such as the Medtronic CareLink® Network developed by Medtronic, plc, of Dublin, Ireland.

In some embodiments, electronic component includes a controller. The controller, which can be any suitable microcontroller or microprocessor, is configured to control the configuration and operation of one or more of the other components of the electronics assembly. For example, the controller may be configured to control the one or more sensors to sense relevant measurement data, to store the measurement data generated by the one or more sensors in the memory. The controller may also be configured to generate message for communication over one or more types of communication interfaces. For example, in the case of RF telemetry communication, the controller generates messages that include the stored data as a payload, packetizes the messages, and provides the message packets to the RF transceiver for transmission to the base station (not shown in FIG. 9). The controller also can be configured to execute commands received from a base station (not shown in FIG. 9) via a communication interface, including e.g., an antenna, a filter, and a RF transceiver. For example, the controller can be configured to receive configuration data from the base station, and to provide the configuration data to the component of the electronics assembly to which the base station directed the configuration data. If the base station directed the configuration data to the controller, then the controller is configured to configure itself in response to the configuration data.

The present disclosure provides the following exemplary embodiments, which are numbered for convenience.

1) A multi-piece implantable joint prosthesis comprising a first piece coupled to an adapter, and a second piece coupled to the adapter, wherein:
    a. the first piece, which may also be referred to as a joint prosthesis component, comprises an electronic component and a first coupler, the electronic component comprising a sensor, the first coupler having a first coupling configuration for coupling to the adapter by a first coupling mechanism;
    b. the second piece, which may also be referred to as a precursor joint prosthesis, comprises a structural component to provide secure engagement with a tissue of a subject in which the prosthesis is implanted, and a fourth coupler having a fourth coupling configuration for coupling to the adapter by a second coupling mechanism; and
    c. the adapter comprises a second coupler having a second coupling configuration for coupling to the first coupler of joint prosthesis component through the first coupling mechanism, and a third coupler having a third coupling configuration for coupling to the fourth coupler of the precursor joint prosthesis through the second coupling mechanism, where the second and third couplers are structurally non-identical.
2) The multi-piece implantable joint prosthesis of embodiment 1, wherein the joint prosthesis component comprises a housing for secure engagement with the tissue of the subject.
3) The multi-piece implantable joint prosthesis of embodiment 1 wherein each of the joint prosthesis component and the precursor joint prosthesis independently provides at least 5% of a surface area of the multi-piece implantable joint prosthesis, or at least 10%, or at least 15%, or at least 20%, or at least 25%, or at least 30% of the surface area of the multi-piece implantable joint prosthesis.
4) The multi-piece implantable joint prosthesis of embodiment 1 wherein the joint prosthesis component, the precursor joint prosthesis and the adapter, taken together, form the entirety of the multi-piece implantable joint prosthesis.
5) The multi-piece implantable joint prosthesis of embodiment 1 wherein any one or more of the first coupler, the second coupler, the third coupler and the fourth coupler is selected from a Morris taper, a threaded rod, a polygonal rod, a cylindrical rod, a Bayonet Neill-Concelman (BNC), and a complement thereof.
6) The multi-piece implantable joint prosthesis of embodiment 1 comprising more than one adapter.
7) The multi-piece implantable joint prosthesis of embodiment 1 wherein the adapter is coupled to the joint prosthesis component and/or to the precursor joint prosthesis by a welded connection.
8) The multi-piece implantable joint prosthesis of embodiment 1 wherein the adapter is coupled to the joint prosthesis component and/or to the precursor joint prosthesis by a threaded connection.
9) The multi-piece implantable joint prosthesis of embodiment 1 wherein adapter is coupled to the joint prosthesis component and/or to the precursor joint prosthesis by a mechanical connection selected from interference fit (also known as press fit, friction fit) and bolting.
10) The multi-piece implantable joint prosthesis of embodiment 1 wherein the adapter is coupled to the joint prosthesis component and/or to the precursor joint prosthesis by adhesive bonding.
11) The multi-piece implantable joint prosthesis of embodiment 1 where the adapter coupled to each of the joint prosthesis component and the precursor joint prosthesis form an implantable joint prosthesis for a joint selected from a hip, knee, ankle, wrist, shoulder, and elbow.
12) The multi-piece implantable joint prosthesis of embodiment 1 which is an implantable joint prothesis selected from a femoral implant for a hip joint and an acetabular implant for a hip joint.
13) The multi-piece implantable joint prosthesis of embodiment 1 which is an implantable joint prosthesis selected from a tibial implant for a knee joint and a femoral implant for a knee joint.
14) The multi-piece implantable joint prosthesis of embodiment 1 which is an implantable joint prosthesis selected from a humeral implant for a shoulder joint and a glenoid implant for a shoulder joint.
15) The multi-piece implantable joint prosthesis of embodiment 1 wherein the sensor is a kinematic sensor, e.g., an accelerometer, and optionally is only one or more accelerometers.
16) The multi-piece implantable joint prosthesis of embodiment 1 wherein the electronic component comprises a communication interface, optionally a wireless communication interface.
17) The multi-piece implantable joint prosthesis of embodiment 1 wherein the electronic component comprises a memory, where the memory may optionally be a memory for storing data obtained from the sensor and/or may optionally be a memory for storing firmware.
18) The multi-piece implantable joint prosthesis of embodiment 1 wherein the electronic component is in electrical communication with a power source.
19) An adapted joint prosthesis component for coupling to a precursor joint prosthesis to provide a multi-piece implantable joint prosthesis, the adapted joint prosthesis component comprising:
    a. a joint prosthesis component comprising a body, a housing that encloses the body, and a first coupler, where a sensor and optionally one or more of a memory, a power supply, and a communication interface are contained within the body, where the first coupler has a first coupling configuration; and
    b. an adapter, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;

c. where the precursor joint prosthesis comprises a fourth coupler having a fourth coupling configuration, where a second coupling mechanism can couple the third coupler of the adapter to the fourth coupler of the precursor joint prosthesis to provide the implantable joint prosthesis.

20) The adapted joint prosthesis component of embodiment 19 wherein the first coupling configuration is different from the third coupling configuration.

21) The adapted joint prosthesis component of embodiment 19 wherein any one or more of the first coupler, the second coupler, the third coupler and the fourth coupler is selected from a Morris taper, a threaded rod, a polygonal rod, a cylindrical rod, a Bayonet Neill-Concelman (BNC), and a complement thereof.

22) The adapted joint prosthesis component of embodiment 19 wherein the first coupling mechanism and/or the second coupling mechanism comprises welding.

23) The adapted joint prosthesis component of embodiment 19 wherein the first coupling mechanism and/or the second coupling mechanism comprises a threaded connection.

24) The adapted joint prosthesis component of embodiment 19 wherein the first coupling mechanism and/or the second coupling mechanism is a mechanical connection selected from interference fit (a.k.a. press fit, friction fit) and bolting.

25) The adapted joint prosthesis component of embodiment 19 wherein the first coupling mechanism and/or the second coupling mechanism is adhesive bonding.

26) The adapted joint prosthesis component of embodiment 19 wherein the multi-piece implantable joint prosthesis is a prosthesis for a joint selected from a hip, knee, ankle, wrist, shoulder, and elbow.

27) The adapted joint prosthesis component of embodiment 19 wherein the multi-piece implantable joint prothesis is selected from a femoral implant for a hip joint and an acetabular implant for a hip joint.

28) The adapted joint prosthesis component of embodiment 19 wherein the multi-piece implantable joint prosthesis is selected from a tibial implant for a knee joint and a femoral implant for a knee joint.

29) The adapted joint prosthesis component of embodiment 19 wherein the multi-piece implantable joint prosthesis is selected from a humeral implant for a shoulder joint and a glenoid implant for a shoulder joint.

30) A precursor joint prosthesis for coupling to an adapted joint prosthesis component to provide a multi-piece implantable joint prosthesis, the precursor joint prosthesis comprising:
   a. a portion of a multi-piece implantable joint prosthesis, where the portion comprises a surface area which is greater than 10% but less than 100% of an entire surface area of the multi-piece implantable joint prosthesis, where the precursor joint prosthesis comprises a fourth coupler having a fourth coupling configuration, where the fourth coupling configuration allows the precursor joint prosthesis to couple to a third coupler having a third coupling configuration of the adapted joint prosthesis component by way of a second coupling mechanism, where the adapted joint prosthesis component comprises b. a joint prosthesis component comprising a body, a housing that encloses the body, and a first coupler, where a sensor and optionally one or more of a memory, a power supply, and a communication interface are contained within the body, where the first coupler has a first coupling configuration; and
   c. an adapter, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
   d. where the precursor joint prosthesis comprises a fourth coupler having a fourth coupling configuration, where a second coupling mechanism can couple the third coupler of the adapter to the fourth coupler of the precursor joint prosthesis to provide the multi-piece implantable joint prosthesis.

31) The precursor joint prosthesis of embodiment 30 wherein the multi-piece implantable joint prosthesis is a prosthesis for a joint selected from a hip, knee, ankle, wrist, shoulder, and elbow.

32) The precursor joint prosthesis of embodiment 30 wherein the multi-piece implantable joint prothesis is selected from a femoral implant for a hip joint and an acetabular implant for a hip joint, and the precursor joint prosthesis provides a portion of a surface area of the femoral implant or the acetabular implant.

33) The precursor joint prosthesis of embodiment 30 wherein the multi-piece implantable joint prosthesis is selected from a tibial implant for a knee joint and a femoral implant for a knee joint, and the precursor joint prosthesis provides a portion of a surface area of the tibial implant or the femoral implant.

34) The precursor joint prosthesis of embodiment 30 wherein the multi-piece implantable joint prosthesis is selected from a humeral implant for a shoulder joint and a glenoid implant for a shoulder joint, and the precursor joint prosthesis provides a portion of a surface area of the humeral implant or the glenoid implant.

35) A multi-piece implantable joint prosthesis comprising an adapted joint prosthesis component coupled to a precursor joint prosthesis, where
   a. the adapted joint prosthesis component comprises:
      i. a joint prosthesis component comprising a body, a housing enclosing the body, and a first coupler, where a sensor and optionally one or more of a memory, a power supply, and a communication interface are contained within the body, where the first coupler has a first coupling configuration; and
      ii. an adapter, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
   where the precursor joint prosthesis comprises:
      iii. a fourth coupler having a fourth coupling configuration, where a second coupling mechanism couples the third coupler of the adapter to the fourth coupler of the precursor joint prosthesis to provide the implantable joint prosthesis, and
      iv. where the precursor joint prosthesis comprises a portion of a surface area of the implantable joint prosthesis which is at least 10% but less than 100% of the surface area of the implantable joint prosthesis.
36) The multi-piece implantable joint prosthesis of embodiment 35 wherein the multi-piece implantable joint prosthesis is a prosthesis for a joint selected from a hip, knee, ankle, wrist, shoulder, and elbow.
37) The multi-piece implantable joint prosthesis of embodiment 35 wherein the multi-piece implantable joint prothesis is selected from a femoral implant for a hip joint and an acetabular implant for a hip joint.
38) The multi-piece implantable joint prosthesis of embodiment 35 wherein the multi-piece implantable joint prosthesis is selected from a tibial implant for a knee joint and a femoral implant for a knee joint.
39) The multi-piece implantable joint prosthesis of embodiment 35 wherein the multi-piece implantable joint prosthesis is selected from a humeral implant for a shoulder joint and a glenoid implant for a shoulder joint.
40) A method of forming a multi-piece implantable joint prosthesis comprising a first piece coupled to an adapter, and a second piece coupled to the adapter, comprising:
 a. providing a first piece, which may also be referred to as a joint prosthesis component, comprises an electronic component and a first coupler, the electronic component comprising a sensor, the first coupler having a first coupling configuration for coupling to the adapter by a first coupling mechanism;
 b. providing a second piece, which may also be referred to as a precursor joint prosthesis, comprises a structural component to provide secure engagement with a tissue of a subject in which the prosthesis is implanted, and a fourth coupler having a fourth coupling configuration for coupling to the adapter by a second coupling mechanism; and
 c. providing an adapter comprising a second coupler having a second coupling configuration for coupling to the first coupler of joint prosthesis component through the first coupling mechanism, and a third coupler having a third coupling configuration for coupling to the fourth coupler of the precursor joint prosthesis through the second coupling mechanism, where the second and third couplers are structurally non-identical;
 d. the method comprising coupling the first piece to the adapter and coupling the second piece to the adapter.
41) The method of embodiment 40, wherein the joint prosthesis component comprises a housing for secure engagement with the tissue of the subject.
42) The method of embodiment 40, wherein each of the joint prosthesis component and the precursor joint prosthesis independently provides at least 5% of a surface area of the multi-piece implantable joint prosthesis, or at least 10%, or at least 15%, or at least 20%, or at least 25%, or at least 30% of the surface area of the multi-piece implantable joint prosthesis.
43) The method of embodiment 40, wherein the joint prosthesis component, the precursor joint prosthesis and the adapter, taken together, form the entirety of the multi-piece implantable joint prosthesis.
44) The method of embodiment 40, wherein any one or more of the first coupler, the second coupler, the third coupler and the fourth coupler is selected from a Morris taper, a threaded rod, a polygonal rod, a cylindrical rod, a Bayonet Neill-Concelman (BNC), and a complement thereof.
45) The method of embodiment 40, wherein the multi-piece implantable joint prostheses comprises more than one adapter.
46) The method of embodiment 40, wherein the adapter is coupled to the joint prosthesis component and/or to the precursor joint prosthesis by a welded connection.
47) The method of embodiment 40, wherein the adapter is coupled to the joint prosthesis component and/or to the precursor joint prosthesis by a threaded connection.
48) The method of embodiment 40, wherein adapter is coupled to the joint prosthesis component and/or to the precursor joint prosthesis by a mechanical connection selected from interference fit (also known as press fit, friction fit) and bolting.
49) The method of embodiment 40, wherein the adapter is coupled to the joint prosthesis component and/or to the precursor joint prosthesis by adhesive bonding.
50) The method of embodiment 40, where the adapter coupled to each of the joint prosthesis component and the precursor joint prosthesis form an implantable joint prosthesis for a joint selected from a hip, knee, ankle, wrist, shoulder, and elbow.
51) The method of embodiment 40, wherein the implantable joint prothesis is selected from a femoral implant for a hip joint and an acetabular implant for a hip joint.
52) The method of embodiment 40, wherein the implantable joint prosthesis is selected from a tibial implant for a knee joint and a femoral implant for a knee joint.
53) The method of embodiment 40, wherein the implantable joint prosthesis is selected from a humeral implant for a shoulder joint and a glenoid implant for a shoulder joint.
54) The method of embodiment 40, wherein the sensor is a kinematic sensor, e.g., an accelerometer, and optionally is only one or more accelerometers.
55) The method of embodiment 40, wherein the electronic component comprises a communication interface, optionally a wireless communication interface.
56) The method of embodiment 40, wherein the electronic component comprises a memory, where the memory may optionally be a memory for storing data obtained from the sensor and/or may optionally be a memory for storing firmware.
57) The method of embodiment 40, wherein the electronic component is in electrical communication with a power source.
58) A method of forming a multi-piece implantable joint prosthesis from an adapted joint prosthesis component and a precursor joint prosthesis, comprising:
 a. providing a joint prosthesis component comprising a body, a housing that encloses the body, and a first coupler, where a sensor and optionally one or more of a memory, a power supply, and a communication interface are contained within the body, where the first coupler has a first coupling configuration; and
 b. providing an adapter, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
 c. where the precursor joint prosthesis comprises a fourth coupler having a fourth coupling configuration, where a second coupling mechanism can couple the third coupler of the adapter to the fourth coupler of the precursor joint prosthesis to provide the implantable joint prosthesis; and the method comprising coupling the adapted joint prosthesis component to the precursor joint prosthesis to provide the multi-piece implantable joint prosthesis.

59) The method of embodiment 58, wherein the first coupling configuration is different from the third coupling configuration.

60) The method of embodiment 58, wherein any one or more of the first coupler, the second coupler, the third coupler and the fourth coupler is selected from a Morris taper, a threaded rod, a polygonal rod, a cylindrical rod, a Bayonet Neill-Concelman (BNC), and a complement thereof.

61) The method of embodiment 58, wherein the first coupling mechanism and/or the second coupling mechanism comprises welding.

62) The method of embodiment 58, wherein the first coupling mechanism and/or the second coupling mechanism comprises a threaded connection.

63) The method of embodiment 58, wherein the first coupling mechanism and/or the second coupling mechanism is a mechanical connection selected from interference fit (a.k.a. press fit, friction fit) and bolting.

64) The method of embodiment 58, wherein the first coupling mechanism and/or the second coupling mechanism is adhesive bonding.

65) The method of embodiment 58, wherein the multi-piece implantable joint prosthesis is a prosthesis for a joint selected from a hip, knee, ankle, wrist, shoulder, and elbow.

66) The method of embodiment 58, wherein the multi-piece implantable joint prothesis is selected from a femoral implant for a hip joint and an acetabular implant for a hip joint.

67) The method of embodiment 58, wherein the multi-piece implantable joint prosthesis is selected from a tibial implant for a knee joint and a femoral implant for a knee joint.

68) The method of embodiment 58, wherein the multi-piece implantable joint prosthesis is selected from a humeral implant for a shoulder joint and a glenoid implant for a shoulder joint.

69) A method of forming a multi-piece implantable joint prosthesis comprising providing a precursor joint prosthesis and providing an adapted joint prosthesis component, the precursor joint prosthesis comprising:
  a. a portion of a multi-piece implantable joint prosthesis, where the portion comprises a surface area which is greater than 10% but less than 100% of an entire surface area of the multi-piece implantable joint prosthesis, where the precursor joint prosthesis comprises a fourth coupler having a fourth coupling configuration, where the fourth coupling configuration allows the precursor joint prosthesis to couple to a third coupler having a third coupling configuration of the adapted joint prosthesis component by way of a second coupling mechanism,
  where the adapted joint prosthesis component comprises
  b. a joint prosthesis component comprising a body, a housing that encloses the body, and a first coupler, where a sensor and optionally one or more of a memory, a power supply, and a communication interface are contained within the body, where the first coupler has a first coupling configuration; and
  c. an adapter, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
  d. where the precursor joint prosthesis comprises a fourth coupler having a fourth coupling configuration, where a second coupling mechanism can couple the third coupler of the adapter to the fourth coupler of the precursor joint prosthesis to provide the multi-piece implantable joint prosthesis;
  the method comprising coupling the precursor joint prosthesis to the adapted joint prosthesis component.

70) The method of embodiment 69, wherein the multi-piece implantable joint prosthesis is a prosthesis for a joint selected from a hip, knee, ankle, wrist, shoulder, and elbow.

71) The method of embodiment 69, wherein the multi-piece implantable joint prothesis is selected from a femoral implant for a hip joint and an acetabular implant for a hip joint, and the precursor joint prosthesis provides a portion of a surface area of the femoral implant or the acetabular implant.

72) The method of embodiment 69, wherein the multi-piece implantable joint prosthesis is selected from a tibial implant for a knee joint and a femoral implant for a knee joint, and the precursor joint prosthesis provides a portion of a surface area of the tibial implant or the femoral implant.

73) The method of embodiment 69, wherein the multi-piece implantable joint prosthesis is selected from a humeral implant for a shoulder joint and a glenoid implant for a shoulder joint, and the precursor joint prosthesis provides a portion of a surface area of the humeral implant or the glenoid implant.

74) A method of forming a multi-piece implantable joint prosthesis comprising coupling an adapted joint prosthesis component to a precursor joint prosthesis, where:
  a. the adapted joint prosthesis component comprises:
    i. a joint prosthesis component comprising a body, a housing enclosing the body, and a first coupler, where a sensor and optionally one or more of a memory, a power supply, and a communication interface are contained within the body, where the first coupler has a first coupling configuration; and
    ii. an adapter, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
  where the precursor joint prosthesis comprises:
    iii. a fourth coupler having a fourth coupling configuration, where a second coupling mechanism couples the third coupler of the adapter to the fourth coupler of the precursor joint prosthesis to provide the implantable joint prosthesis, and
    iv. where the precursor joint prosthesis comprises a portion of a surface area of the implantable joint prosthesis which is at least 10% but less than 100% of the surface area of the implantable joint prosthesis.

75) The method of embodiment 74, wherein the multi-piece implantable joint prosthesis is a prosthesis for a joint selected from a hip, knee, ankle, wrist, shoulder, and elbow.
76) The method of embodiment 74, wherein the multi-piece implantable joint prothesis is selected from a femoral implant for a hip joint and an acetabular implant for a hip joint.
77) The method of embodiment 74, wherein the multi-piece implantable joint prosthesis is selected from a tibial implant for a knee joint and a femoral implant for a knee joint.
78) The method of embodiment 74, wherein the multi-piece implantable joint prosthesis is selected from a humeral implant for a shoulder joint and a glenoid implant for a shoulder joint.
79) A multi-piece implantable joint prosthesis comprising a first piece coupled to a second piece, wherein:
   a. the first piece, which may also be referred to as a joint prosthesis component, comprises an electronic component and a first coupler, the electronic component comprising a sensor, the first coupler having a first coupling configuration for coupling to the second piece by a first coupling mechanism;
   b. the second piece, which may also be referred to as a precursor joint prosthesis, comprises a structural component to provide secure engagement with a tissue of a subject in which the prosthesis is implanted, and a fourth coupler having a fourth coupling configuration for coupling to the first piece by the first coupling mechanism.
80) The multi-piece implantable joint prosthesis of claim 79 wherein the second piece is a portion of a femoral component, a humeral component, or a partial knee component of a prothesis for a total or partial joint arthroplasty, and the second component is an electronic component comprising a sensor.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is also to be understood that as used herein and in the appended claims, the singular forms "a," "an," and "the" include plural reference unless the context clearly dictates otherwise, the term "X and/or Y" means "X" or "Y" or both "X" and "Y," and the letter "s" following a noun designates both the plural and singular forms of that noun. In addition, where features or aspects of the present disclosure are described in terms of Markush groups, it is intended, and those skilled in the art will recognize, that the present disclosure embraces and is also thereby described in terms of any individual member and any subgroup of members of the Markush group, and Applicants reserve the right to revise the application or claims to refer specifically to any individual member or any subgroup of members of the Markush group.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. For example, the term "a sensor" refers to one or more sensors, and the term "a medical device comprising a sensor" is a reference to a medical device that includes at least one sensor, where the medical device comprising a sensor may have, for example, 1 sensor, 2 sensors, 3 sensors, 4 sensors, 5 sensors, 6 sensors, 7 sensors, 8 sensors, 9 sensors, 10 sensors, or more than 10 sensors. A plurality of sensors refers to more than one sensor. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include," as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the disclosure, invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the disclosure, invention or claims. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Included as being incorporated by reference are each of PCT/US2020/036516, PCT/US2017/023916 and PCT/US2015/050789. Such documents may be incorporated by reference for the purpose of describing and disclosing, for example, materials and methodologies described in the publications, which might be used in connection with the present disclosure. The publications discussed above and throughout the text are provided solely for their disclosure prior to the filing date of the present application. Nothing herein is to be construed as an admission that the inventors are not entitled to antedate any referenced publication by virtue of prior invention.

All patents, publications, scientific articles, web sites, and other documents and materials referenced or mentioned herein are indicative of the levels of skill of those skilled in the art to which the disclosure pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A multi-piece implantable joint prosthesis comprising a first piece coupled to an adapter, and a second piece coupled to the adapter, wherein:
    a) the first piece is configured to fit into a bone cavity, and comprises an electronic component and a first coupler, the electronic component comprising a sensor, the first coupler having a first coupling configuration for coupling to the adapter by a first coupling mechanism;
    b) the second piece comprises a structural component to provide secure engagement with a tissue of a subject in which the second piece is implanted, and a fourth coupler configured to fit into the bone cavity, and having a fourth coupling configuration for coupling to the adapter by a second coupling mechanism; and
    c) the adapter is configured to fit into the bone cavity, and comprises a second coupler having a second coupling configuration for coupling to the first coupler of joint prosthesis component through the first coupling mechanism, and a third coupler having a third coupling configuration for coupling to the fourth coupler of the second piece through the second coupling mechanism, where the second and third couplers are structurally non-identical.

2. An adapted joint prosthesis component for coupling to a precursor joint prosthesis to provide a multi-piece implantable joint prosthesis, the adapted joint prosthesis component configured to fit into a bone cavity, and comprising:
    a) a joint prosthesis component configured to fit into a bone cavity, and comprising a body and a first coupler, where a sensor and one or more of a memory, a power supply, and a communication interface are contained within the body, where the first coupler has a first coupling configuration; and
    b) an adapter configured to fit into bone cavity, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
    c) where the precursor joint prosthesis comprises a fourth coupler configured to fit into the bone cavity, and having a fourth coupling configuration, where a second coupling mechanism can couple the third coupler of the adapter to the fourth coupler of the precursor joint prosthesis to provide the multi-piece implantable joint prosthesis.

3. A precursor joint prosthesis for coupling to an adapted joint prosthesis component to provide a multi-piece implantable joint prosthesis, the precursor joint prosthesis comprising:
   a) a portion of a multi-piece implantable joint prosthesis, where the portion comprises a surface area which is greater than 10% but less than 100% of an entire surface area of the multi-piece implantable joint prosthesis, where the precursor joint prosthesis comprises a fourth coupler configured to fit into a bone cavity, the fourth coupler having a fourth coupling configuration, where the fourth coupling configuration allows the precursor joint prosthesis to couple to a third coupler having a third coupling configuration of the adapted joint prosthesis component by way of a second coupling mechanism,
   where the adapted joint prosthesis component comprises
   b) a joint prosthesis component configured to fit into the bone cavity, and comprising a body and a first coupler, where a sensor and one or more of a memory, a power supply, and a communication interface are contained within the body, where the first coupler has a first coupling configuration; and
   c) an adapter configured to fit into the bone cavity, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
   d) where a second coupling mechanism can couple the third coupler of the adapter to the fourth coupler of the precursor joint prosthesis to provide the multi-piece implantable joint prosthesis.

4. A multi-piece implantable joint prosthesis comprising an adapted joint prosthesis component coupled to a precursor joint prosthesis, where
   a) the adapted joint prosthesis component is configured to fit into a bone cavity, and comprises:
      i) a joint prosthesis component configured to fit into the bone cavity, and comprising a body and a first coupler, where a sensor and one or more of a memory, a power supply, and a communication interface are contained within the body, where the first coupler has a first coupling configuration; and
      ii) an adapter configured to fit into the bone cavity, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
   b) where the precursor joint prosthesis comprises:
      i) a fourth coupler configured to fit into the bone cavity, and having a fourth coupling configuration, where a second coupling mechanism couples the third coupler of the adapter to the fourth coupler of the precursor joint prosthesis to provide the multi-piece implantable joint prosthesis, and
      ii) where the precursor joint prosthesis comprises a portion of a surface area of the multi-piece implantable joint prosthesis which is at least 10% but less than 100% of the surface area of the multi-piece implantable joint prosthesis.

5. A method of forming a multi-piece implantable joint prosthesis comprising a first piece coupled to an adapter, and a second piece coupled to the adapter, comprising:
   a) providing a first piece configured to fit into a bone cavity, and that comprises an electronic component and a first coupler, the electronic component comprising a sensor, the first coupler having a first coupling configuration for coupling to the adapter by a first coupling mechanism;
   b) providing a second piece comprises a structural component to provide secure engagement with a tissue of a subject in which the second piece is implanted, and a fourth coupler configured to fit into the bone cavity, and having a fourth coupling configuration for coupling to the adapter by a second coupling mechanism; and
   c) providing an adapter configured to fit into the bone cavity, and comprising a second coupler having a second coupling configuration for coupling to the first coupler of joint prosthesis component through the first coupling mechanism, and a third coupler having a third coupling configuration for coupling to the fourth coupler of the second piece through the second coupling mechanism, where the second and third couplers are structurally non-identical;
   the method comprising coupling the first piece to the adapter and coupling the second piece to the adapter.

6. A method of forming a multi-piece implantable joint prosthesis from an adapted joint prosthesis component configured to fit into a bone cavity and a precursor joint prosthesis, comprising:
   a) providing a joint prosthesis component configured to fit into the bone cavity, and comprising a body and a first coupler, where a sensor and one or more of a memory, a power supply, and a communication interface are contained within the body, where the first coupler has a first coupling configuration; and
   b) providing an adapter configured to fit into the bone cavity, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
   c) where the precursor joint prosthesis comprises a fourth coupler configured to fit into the bone cavity, and having a fourth coupling configuration, where a second coupling mechanism can couple the third coupler of the adapter to the fourth coupler of the precursor joint prosthesis to provide the multi-piece implantable joint prosthesis; and
   the method comprising coupling the adapted joint prosthesis component to the precursor joint prosthesis to provide the multi-piece implantable joint prosthesis.

7. A method of forming a multi-piece implantable joint prosthesis comprising providing a precursor joint prosthesis and providing an adapted joint prosthesis component, the precursor joint prosthesis comprising:
   a) a portion of a multi-piece implantable joint prosthesis, where the portion comprises a surface area which is greater than 10% but less than 100% of an entire surface area of the multi-piece implantable joint prosthesis, where the precursor joint prosthesis comprises a fourth coupler configured to fit into a bone cavity, the fourth coupler having a fourth coupling configuration, where the fourth coupling configuration allows the precursor joint prosthesis to couple to a third coupler having a third coupling configuration of the adapted joint prosthesis component by way of a second coupling mechanism,
where the adapted joint prosthesis component is configured to fit into the bone cavity comprises
b) a joint prosthesis component configured to fit into the bone cavity, and comprising a body and a first coupler, where a sensor one or more of a memory, a power supply, and a communication interface are contained within the body, where the first coupler has a first coupling configuration; and
c) an adapter configured to fit into the bone cavity, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
d) where a second coupling mechanism can couple the third coupler of the adapter to the fourth coupler of the precursor joint prosthesis to provide the multi-piece implantable joint prosthesis;
the method comprising coupling the precursor joint prosthesis to the adapted joint prosthesis component.

8. A method of forming a multi-piece implantable joint prosthesis comprising coupling an adapted joint prosthesis component to a precursor joint prosthesis, where:
a) the adapted joint prosthesis component is configured to fit into a bone cavity, and comprises:
  i) a joint prosthesis component is configured to fit into the bone cavity, and comprising a body and a first coupler, where a sensor and optionally one or more of a memory, a power supply, and a communication interface are contained within the body, where the first coupler has a first coupling configuration; and
  ii) an adapter configured to fit into the bone cavity, the adapter comprising a second coupler having a second coupling configuration, and a third coupler having a third coupling configuration, where a first coupling mechanism couples the first coupler of the joint prosthesis component to the second coupler of the adapter to provide the adapted joint prosthesis component;
b) where the precursor joint prosthesis comprises:
  i) a fourth coupler configured to fit into the bone cavity, and having a fourth coupling configuration, where a second coupling mechanism couples the third coupler of the adapter to the fourth coupler of the precursor joint prosthesis to provide the multi-piece implantable joint prosthesis, and
  ii) where the precursor joint prosthesis comprises a portion of a surface area of the multi-piece implantable joint prosthesis which is at least 10% but less than 100% of the surface area of the multi-piece implantable joint prosthesis.

\* \* \* \* \*

UNITED STATES PATENT AND TRADEMARK OFFICE
CERTIFICATE OF CORRECTION

PATENT NO. : 12,090,066 B1  
APPLICATION NO. : 17/589728  
DATED : September 17, 2024  
INVENTOR(S) : Jeffrey M. Gross Page 1 of 1

It is certified that error appears in the above-identified patent and that said Letters Patent is hereby corrected as shown below:

In the Claims

Claim 1(c), Column 42, Lines 37-38:
Delete "of joint prosthesis component"

Signed and Sealed this  
Ninth Day of December, 2025

John A. Squires  
*Director of the United States Patent and Trademark Office*